(12) United States Patent
Comando

(10) Patent No.: US 10,593,527 B1
(45) Date of Patent: Mar. 17, 2020

(54) DETECTION AND CONCENTRATION DETERMINATION OF 2,3,3,3-TETRAFLUORO-2-(1,1,2,2,3,3,3-HEPTAFLUOROPROPOXY) PROPANOIC ACID BY LC/MS/MS

(71) Applicant: Suffolk County Water Authority, Oakdale, NY (US)

(72) Inventor: Amanda Comando, Smithtown, NY (US)

(73) Assignee: Suffolk County Water Authority, Oakdale, NY (US)

( * ) Notice: Subject to any disclaimer, the term of this patent is extended or adjusted under 35 U.S.C. 154(b) by 0 days.

(21) Appl. No.: 16/225,363

(22) Filed: Dec. 19, 2018

(51) Int. Cl.
*H01J 49/00* (2006.01)
*G01N 30/72* (2006.01)
*H01J 49/04* (2006.01)
*G01N 30/30* (2006.01)

(52) U.S. Cl.
CPC .......... *H01J 49/0031* (2013.01); *G01N 30/30* (2013.01); *G01N 30/7233* (2013.01); *H01J 49/045* (2013.01); *H01J 49/0468* (2013.01)

(58) Field of Classification Search
CPC .. H01J 49/0031; H01J 49/0468; H01J 49/045; G01N 30/7233; G01N 30/30
USPC ........................................ 250/281, 282, 288
See application file for complete search history.

(56) References Cited

U.S. PATENT DOCUMENTS

2009/0294660 A1* 12/2009 Whitehouse .......... H01J 49/045
250/288

OTHER PUBLICATIONS

Huset et al., "Quantitative Determination of Perfluoroalkyl Substanace (PFAS) in Soil, Water, and Home Garden Produce", MethodsX, Elsevier, pp. 697-704. (2018).

* cited by examiner

*Primary Examiner* — Michael Maskell
(74) *Attorney, Agent, or Firm* — Heslin Rothenberg Farley & Mesiti P.C.; Adolph Bohnstedt

(57) ABSTRACT

A method and system for injecting an unconcentrated sample into a receiving LC/MS/MS system that is configured to determine a concentration of GenX within the unconcentrated sample, wherein the LC/MS/MS includes ESI. The unconcentrated sample is subjected to the following ESI conditions: i) a probe gas temperature of approximately 120° C. to approximately 160° C.; ii) a sheath gas heater setting of approximately 150° C. to approximately 275° C.; and iii) a sheath gas flow of approximately 6 L/min to approximately 11 L/min. The concentration of GenX is determined within the unconcentrated sample, wherein the concentration of GenX within the unconcentrated sample has a minimum reporting level of approximately 0.010 µg/L.

20 Claims, 2 Drawing Sheets

DETECTION AND CONCENTRATION DETERMINATION OF 2,3,3,3-TETRAFLUORO-2-(1,1,2,2,3,3,3-HEPTAFLUOROPROPOXY) PROPANOIC ACID BY LC/MS/MS

FIELD OF THE INVENTION

Embodiments of the present invention relate to qualitative and quantitative analysis of analytes in samples and more particularly to the qualitative and quantitative analysis of 2,3,3,3-tetrafluoro-2-(1,1,2,2,3,3,3-heptafluoropropoxy) propanoic acid in water.

BACKGROUND

The fluorochemical 2,3,3,3-tetrafluoro-2-(1,1,2,2,3,3,3-heptafluoropropoxy) propanoic acid ("GenX acid" or simply "GenX") is employed in a process (i.e., the "GenX process") that has been used in products such as food packaging, paints, cleaning products, non-stick coatings, outdoor fabrics and firefighting foam. The GenX process was developed to replace processes that produced other per- and polyfluoroalkyl substances (PFAS) such as perfluorooctanoic acid (PFOA) and perfluorooctanesulfonate (PFOS). Most US industries have phased out production of PFOA and PFOS because of concerns about health risks to humans and, instead, have employed processes that employ alternative PFAS, such as GenX. Although there is a substantial body of knowledge regarding health risks from older PFAS like PFOS and PFOA, there is much less knowledge about the health risks associated with new PFAS like GenX.

Recently, GenX has been detected in Cape Fear River near Wilmington, N.C., presumably originating from a plant employing the GenX process upstream from Wilmington. Because of concerns regarding the yet unknown health risks to humans exposed to GenX, this event has triggered significant interest in finding inexpensive and sensitive methods for detecting GenX in other public water sources that are near plants that employ the GenX process.

SUMMARY OF INVENTION

Shortcomings of the prior art are overcome and additional advantages are provided through the provision of a method and system for detecting GenX in a solution or an unconcentrated sample.

The method includes injecting an unconcentrated sample into a receiving LC/MS/MS (liquid chromatography/tandem mass spectroscopy) system, which is configured to determine a concentration of GenX within the unconcentrated sample, wherein the LC/MS/MS includes electrospray ionization (ESI); subjecting the unconcentrated sample to the following ESI conditions: i) a probe gas temperature of approximately 120° C. to approximately 160° C., ii) a sheath gas heater setting of approximately 150° C. to approximately 275° C., and iii) a sheath gas flow of approximately 6 L/min to approximately 11 L/min; and determining the concentration of GenX within the unconcentrated sample, wherein the concentration of GenX within the unconcentrated sample is at least approximately 0.010 µg/L.

The system includes an LC/MS/MS system operable utilizing ESI and configured to receive an injection of an unconcentrated sample containing GenX. The LC/MS/MS system subjects the unconcentrated sample to the following ESI conditions: i) a probe gas temperature of approximately 120° C. to approximately 160° C.; ii) a sheath gas heater setting of approximately 150° C. to approximately 275° C.; and iii) a sheath gas flow of approximately 6 L/min to approximately 11 L/min. The LC/MS/MS system determines a concentration of GenX within the unconcentrated sample, wherein the concentration of GenX within the unconcentrated sample is at least approximately 0.010 µg/L.

In an embodiment, the concentration of GenX within the unconcentrated sample is between approximately 0.010 µg/L to approximately 1.0 µg/L. In an embodiment, the unconcentrated sample is subjected to the following ESI conditions: i) a probe gas temperature of approximately 120° C.; ii) a sheath gas heater setting of approximately 150° C.; and iii) a sheath gas flow of approximately 6 L/min. In this embodiment, the ESI conditions may also include: i) a negative ion polarity setting; ii) a gas flow setting of approximately 11 L/min; iii) a nebulizer setting of 20 psi; iv) a capillary voltage setting of approximately 3000 V; v) a voltage charging setting of 0; and vi) the following ion-funnel parameters: high pressure RF=90 and low pressure RF=60. When these conditions are configured, the method/system may detect GenX within a second unconcentrated sample, wherein a second concentration of GenX within the second unconcentrated sample is at least approximately 0.0022 µg/L. In an embodiment, an amount of GenX in a single injection of unconcentrated sample is at least approximately $7.5 \times 10^{-7}$ µg. In an embodiment, an amount of GenX in a single injection of unconcentrated sample is between approximately $7.5 \times 10^{-7}$ µg to approximately $7.5 \times 10^{-5}$ µg.

The method further includes injecting a solution containing GenX into an LC/MS/MS system that is configured to detect GenX within the solution, wherein the LC/MS/MS includes ESI; subjecting a GenX-containing LC eluent of the solution to the following ESI conditions: i) a probe gas temperature of approximately 120° C. to approximately 160° C., ii) a sheath gas heater setting of approximately 150° C. to approximately 275° C., and iii) a sheath gas flow of approximately 6 L/min to approximately 11 L/min; and determining a concentration of GenX within the solution containing GenX, wherein an injected amount of GenX within the solution containing GenX is at least approximately $7.5 \times 10^{-7}$ µg.

The system further includes an LC/MS/MS system operable utilizing ESI and configured to receive an injection of a solution containing GenX. The LC/MS/MS system subjects a GenX-containing LC eluent of the solution to the following ESI conditions: i) a probe gas temperature of approximately 120° C. to approximately 160° C.; ii) a sheath gas heater setting of approximately 150° C. to approximately 275° C.; and iii) a sheath gas flow of approximately 6 L/min to approximately 11 L/min. The LC/MS/MS system determines a concentration of GenX within the solution containing GenX, wherein a received injected amount of GenX within the solution containing GenX is at least approximately $7.5 \times 10^{-7}$ µg.

In an embodiment, the injected amount of GenX within the solution containing GenX is between approximately $7.5 \times 10^{-7}$ µg to approximately $7.5 \times 10^{-5}$ µg. In an embodiment, the GenX-containing eluent is subjected to the following ESI conditions: i) a probe gas temperature of approximately 120° C.; ii) a sheath gas heater setting of approximately 150° C.; and iii) a sheath gas flow of approximately 6 L/min. In this embodiment, the ESI conditions may also include: i) a negative ion polarity setting; ii) a gas flow setting of approximately 11 L/min; iii) a nebulizer setting of 20 psi; iv) a capillary voltage setting of approximately 3000 V; v) a voltage charging setting of 0; and vi) the following ion-funnel parameters: high pressure RF=90 and low pressure RF=60. When these conditions are configured, the method/system may detect GenX within a second injected solution containing GenX, wherein a second amount of GenX within the second injected solution is at least approximately $1.7 \times 10^{-7}$ μg. In an embodiment, the GenX concentration is determined to be at least approximately 0.010 μg/L when approximately 75 μL of the solution containing GenX is injected into the LC/MS/MS system. In an embodiment, GenX is detected at a concentration of at least approximately 0.022 μg/L when approximately 75 μL of the second solution containing GenX is injected into the LC/MS/MS system.

In an embodiment, the unconcentrated sample and solution are aqueous unconcentrated samples and solutions, respectively. In this embodiment, the aqueous unconcentrated sample and solution are selected from: finished drinking water, ground water, raw source water, and water at an intermediate stage of treatment between raw source water and finished drinking water.

DETAILED DESCRIPTION

Figure 1:
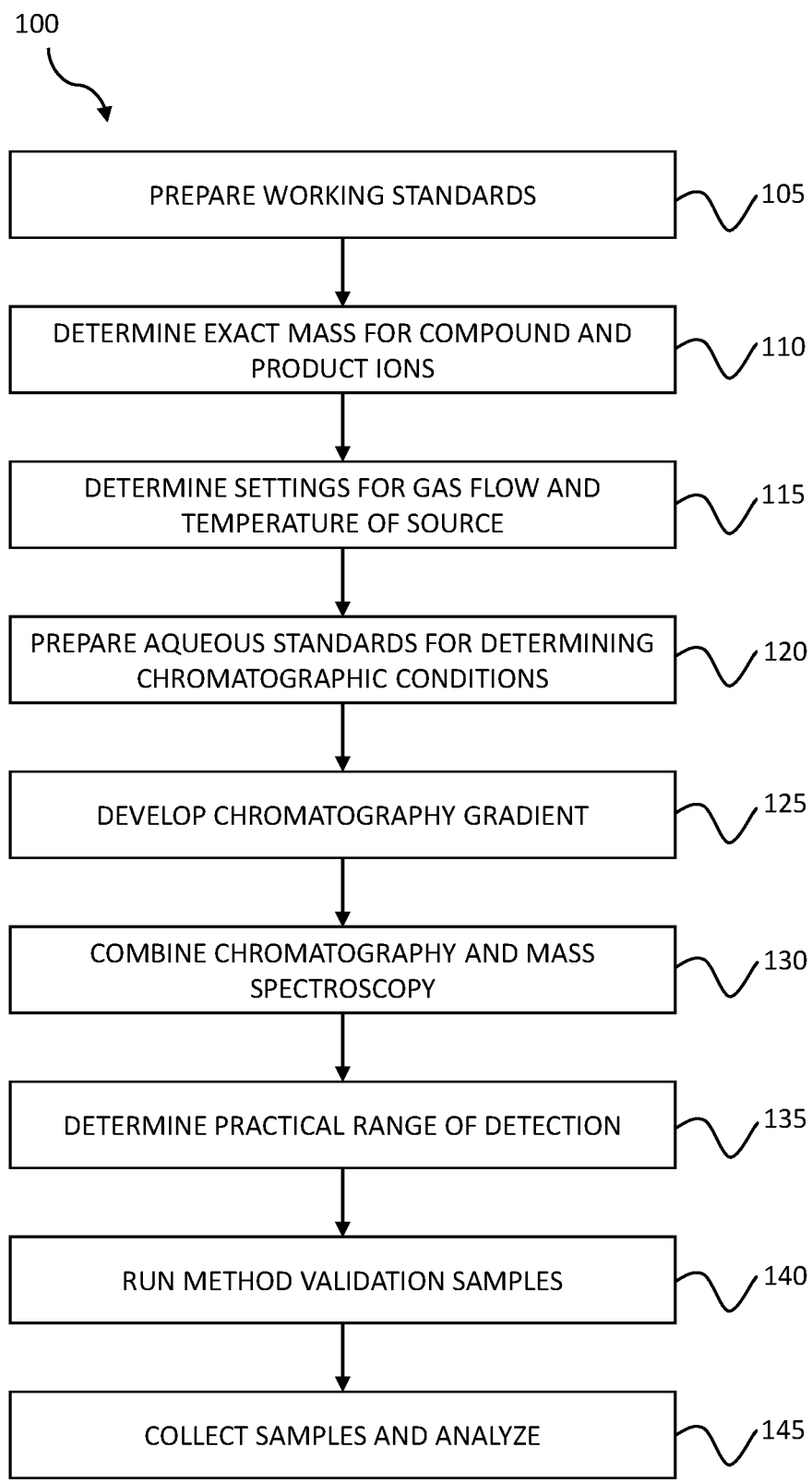
FIG. 1 illustrates processes for validating a method to determine levels of GenX in samples, in accordance with an exemplary embodiment of the present invention.

Currently, the quantitative determination of low levels of the analyte GenX in water sources requires extraction of the GenX from the water due to the limitations of the analytical methods employed for sample analysis. When analyte concentrations are too low to be quantitated, extraction thereof serves to provide a more concentrated sample than the collected unconcentrated water sample. These extraction steps are often time-consuming, costly, and inherently introduce the possibility of errors in the analysis. In some cases, up to one liter of water from a contaminated water source must be extracted to provide 1 mL of an aqueous sample after evaporation of extracting solvent and subsequent aqueous dissolution of the isolated extract. Furthermore, detection of GenX by liquid chromatography/tandem mass spectroscopy (LC/MS/MS) is impeded by the instability of GenX during ionization compared to other PFAS. This instability results in the breakdown of the compound, which makes it difficult to easily detect GenX and quantitate its concentration.

Embodiments of the present invention recognize that extraction steps contribute to increased costs and errors in the qualitative and quantitative analysis of GenX in water samples. Embodiments of the present invention recognize that typical ionization conditions, which provide quantitative analysis of PFAS such as PFOA and PFOS, lead to complex fragmentation of GenX samples; this makes the detection and concentration determination of GenX in aqueous samples difficult, if not impossible. Embodiments of the present invention provide a method and LC/MS/MS system for the detection and concentration determination of low levels of GenX in unconcentrated as well as concentrated samples. In the case of unconcentrated samples, such as finished drinking water, ground water, raw source water, and water at an intermediate stage of treatment between raw source water and finished drinking water, extraction techniques are avoided. Embodiments of the present invention provide electrospray ionization (ESI) conditions that avoid complex fragmentation of injected GenX unconcentrated and concentrated samples, thereby making said GenX samples readily subject to low-level GenX detection and concentration determination.

Certain exemplary embodiments will now be described to provide an overall understanding of the principles of the structure, function, and use of the methods and systems disclosed herein. One or more examples of these embodiments are illustrated in the accompanying drawings. Those skilled in the art will understand that the methods and systems specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "substantially", "approximately", "about", "relatively," or other such similar terms that may be used throughout this disclosure, including the claims, are used to describe and account for small fluctuations, such as due to variations in processing. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

In various embodiments, unconcentrated samples are analyzed for detection and quantitation of the analyte GenX. As used herein, "unconcentrated sample" typically refers to an aqueous sample collected from a water source such as, but not limited to, finished drinking water, ground water, raw source water, and water at an intermediate stage of treatment between raw source water and finished drinking water. The sample may also be collected from an effluent from processes that utilize GenX, such as from a factory that produces GenX-containing products. The unconcentrated sample is not concentrated by any deliberate or substantial evaporation of the solvent, i.e., water. Further, the unconcentrated sample is not concentrated by, for example, extraction into an organic solvent to subsequently make a non-aqueous or aqueous solution of GenX that has higher concentration than the originally collected sample. An unconcentrated sample also includes a sample that is diluted with respect to the originally collected sample. The diluent may be water or a water-miscible solvent such as, but not limited to, an alcohol (e.g., methanol, ethanol, n-propanol, isopropanol, n-butanol sec-butanol, iso-butyl alcohol, tert-butyl alcohol, diols such as ethylene glycol, triols such as glycerol, etc.), acetonitrile, dimethylformamide, dimethyl sulfoxide, dimethylacetamide, etc. In some embodiments, unconcentrated samples also contain added chemicals, such as ammonium chloride for purposes of dechlorination.

Unconcentrated samples include such water samples which are not diluted or concentrated such that they may be directly injected into the system for analysis.

In various embodiments, concentrated samples are analyzed for detection and quantitation of GenX at extremely low levels. As used herein, "concentrated samples" include samples obtained via one or more of the following steps: i) the extraction of GenX from a first volume of water (typically an aqueous sample obtained directly from a water source) into second volume of a water-immiscible solvent, wherein the second volume of a water-immiscible solvent is less than, substantially the same, or greater than the first volume of water; ii) partial or complete evaporation of the water-immiscible solvent to concentrate the GenX contained therein; and iii) re-dissolving the GenX analyte into a third volume of water with or without the concomitant introduction of preservatives and/or dechlorination agents, wherein the third volume of water is of a lesser volume than the first volume of water.

In some embodiments of the present invention, concentrated and unconcentrated samples of GenX include samples collected and prepared from soil and plants, as described elsewhere for PFAS that do not include GenX (e.g., see Huset and Barry, "Quantitative determination of perfluoroalkyl substances (PFAS) in soil, water, and home garden produce", *MethodsX* 5 (2018) 697-704). In some embodiments, concentrated and unconcentrated samples of GenX include samples collected from urine and blood.

As used herein, the term "GenX solution," "GenX in a solution," "a solution containing GenX," etc. includes a homogeneous solution of GenX, which includes concentrated and unconcentrated GenX samples as well as standards, etc. As is well-known in the art, for any analyte to be injected onto an LC/MS/MS system, it must be in a homogeneous solution of a solvent suitable for injection onto an LC column.

It is understood that within a known volume of an analyte solution that has a known concentration, the amount of analyte is also known and readily calculated. For example, 75 microliters (μL or μl) of a GenX solution that has a concentration of 0.010 micrograms per liter (μg/L or μg/l) contains $7.5 \times 10^{-7}$ μg of GenX according to the equation: $(0.010\ \mu g/L) \times (75\ \mu L) \times (10^{-6}\ L/\mu L) = 7.5 \times 10^{-7}$ μg. Thus, 75 μL of a 0.0022 μg/L solution of GenX contains $1.7 \times 10^{-7}$ μg of GenX and 75 μL of a 1.0 μg/L solution of GenX contains $7.5 \times 10^{-5}$ μg of GenX. Herein, any known volume of an analyte solution with a known concentration may be expressed in terms of a known mass of analyte.

Herein, analyte concentration may be expressed as parts per trillion (ppt) according to the relationship 1 ng/L=1 ppt. Thus, 0.010 μg/L may be expressed as 10 ppt, 0.0022 μg/L may be expressed as 2.2 ppt, and 1.0 μg/L may be expressed as 1000 ppt. Because the relationship between ppt and μg/L is known, a known volume containing a known ppt of an analyte may also be expressed in terms of a known mass of the analyte.

Embodiments of the present invention will now be described in detail with reference to FIG. 1.

FIG. 1 illustrates processes, generally designated 100, for validating a method to determine levels of GenX in samples in accordance with an exemplary embodiment of the present invention.

Table 1 abbreviations are used in various tables referred to throughout FIG. 1.

TABLE 1

| Abbreviations | |
|---|---|
| WS | Working Standard(s) |
| ICS | Initial Calibration Standard(s) |
| CCV | Continuing Calibration Verification standard(s) |
| CCV HL | Continuing Calibration Verification standard High Level |
| CCV LL | Continuing Calibration Verification standard Low Level |
| CCV ML | Continuing Calibration Verification standard Medium Level |
| LFB | Laboratory Fortified Blank(s) |
| LFBML | Laboratory Fortified Blank Medium Level |
| LFM | Laboratory Fortified Matrix standard(s) |
| LFM ML | Laboratory Fortified Matrix standard Medium Level |
| LFMD | Laboratory Fortified Matrix Duplicate standard(s) |
| QC | Quality Control |
| QCS | Quality Control Sample |

TABLE 1-continued

| Abbreviations | |
|---|---|
| PDS | Primary Dilution Standard |
| SS | Stock Standard |
| PRW | Preserved Reagent Water |
| MB | Method Blank |
| IS | Internal Standard |
| IDC | Initial Demonstration of Capability |
| DOC | Demonstration of Capability |
| MDL | Method Detection Limit |
| RDL | Required Detection Limit |
| MRL | Minimum Reporting Level |
| RL | Reporting Limit |

In step 105, working standards (WS) of the analyte GenX are prepared. In various embodiments, working standards are instrument calibration, calibration verification, and quality control standards analyzed in an analytical run such as an initial calibration standard (ICS), a continuing calibration verification (CCV) standard, a laboratory fortified blank (LFB), a laboratory fortified matrix (LFM) standard, a laboratory fortified matrix duplicate (LFMD) standard, a quality control sample (QCS), etc.

An initial calibration standard includes a solution prepared from the primary dilution standard solution (PDS) or stock standard (SS) solutions. The initial calibration standard solutions are used to calibrate an instrument response with respect to an analyte concentration.

A continuing calibration verification includes a calibration standard containing a specified concentration of method analytes, which is analyzed at specified periods to verify an accuracy of the existing calibration for said analytes.

A laboratory fortified blank is an aliquot of preserved reagent water (PRW) to which known quantities of the method analytes are added in the laboratory. In various embodiments, the laboratory fortified blank is analyzed using the same protocol as a sample. In some embodiments, the purpose of the laboratory fortified blank is to determine whether the method is valid, and whether the method can make accurate and precise measurements with respect to a specified criterion. For some embodiments of the present invention, there is no substantially significant difference between a laboratory fortified blank and a continuing calibration verification standard.

Preserved reagent water is a solution comprising approximately 200 mg/L ammonium chloride solution in deionized water, which is typically prepared monthly. Deionized water is water having a resistance of approximately 18.2 Megaohms/cm or greater because of deionization.

A laboratory fortified matrix standard is an aliquot of an environmental sample to which known quantities of method analytes are added in the laboratory. The laboratory fortified matrix standard is analyzed like a sample, and its purpose is to determine whether the sample matrix contributes bias to the analytical results. The background concentrations of the analytes in the sample matrix should preferably be determined in a separate aliquot and the measured values in the laboratory fortified matrix standard corrected for background concentrations. In various embodiments, a laboratory fortified matrix duplicate standard is a second aliquot of an environmental sample used to prepare the laboratory fortified matrix standard. The laboratory fortified matrix duplicate standard is fortified, processed, and analyzed in the same way as the laboratory fortified matrix standard. The laboratory fortified matrix standard duplicate is used instead of a laboratory duplicate to assess method precision when the occurrence of target analytes is low.

A quality control sample is a solution of method analytes obtained from a source external to the laboratory and different from the source of calibration standards. The quality control sample is used to verify the accuracy of the calibration standards.

A primary dilution standard is a solution of one or several analytes prepared in the laboratory from stock standard solutions and diluted as needed to prepare calibration solutions and other needed analyte solutions. Primary dilution standards are prepared at concentrations that are suitable for secondary or working standard preparation. Primary dilution standards are typically stored in the refrigerator at ≤4° C. with expiration dates of 3 months. The standard identification, preparation date, expiration date and analyst initials are written on the label. The expiration date of the prepared standard typically does not exceed the expiration date provided by the vendor in its certificate of analysis.

A stock standard is a concentrated solution containing one or more method analytes prepared in the laboratory using assayed reference materials or purchased as certified from the reputable commercial source. Certified standards are used to prepare primary dilution standards, secondary dilution standards and working standards. In various embodiments, if certified standards are not available, the solid compounds are obtained from the manufacturer. In these embodiments, if compounds used to prepare solutions are 96% pure or greater, the solid weight is used without correction for purity to calculate the concentration of the stock standard.

Method blanks are aliquots of preserved reagent water that are treated exactly as a sample including exposure to all glassware, equipment, solvents, reagents, etc. method blanks are used with other samples. In various embodiments, the method blanks are used to determine if method analytes or other interferences are present in the laboratory environment, the reagents, or the apparatus.

An internal standard is a pure compound added to a standard solution in a known amount and used to measure the relative response of the method analyte. In some embodiments, the internal standard includes isotopically labeled analogues (e.g., $^{13}C$) of method analyte.

An analysis batch is a set of up to 20 field samples (not including quality control samples such as method blanks, continuing calibration verification standards, laboratory fortified matrix standards and laboratory fortified matrix duplicate standards) that are analyzed on the same instrument during a 24-hour period that begins and ends with the analysis of the appropriate continuing calibration verification standard. In some embodiments, an additional continuing calibration verification standard is required after analysis of 10 field samples.

In general, working standards are obtained from materials purchased from vendors and any products made with TEFLON® are avoided when the analytes being tested for include PFAS such as GenX.

Table 2 shows an example of a preparation of stock standards and primary dilution standards for GenX:

TABLE 2

Example of Preparation of Stock Standards and Primary Dilution for GenX.

| | Stock Standard Custom Mix-SS | | | | Primary dilution Standards PDS | | | |
|---|---|---|---|---|---|---|---|---|
| Mix description | Analyte Name | Weight [g] | Volume and Solvent [mL] | Conc. µg/ml | Volume of SS used [µL] | Conc [µg/mL] | Final Volume/ Solvent [mL] | Code |
| Wellington Labs individual compounds | GenX | NA | NA | 50.0 | 50.0 | 0.10 | 25.00 | PDS |
| | $^{13}C$-GenX | NA | NA | 50.0 | 25.0 | 0.050 | 25.00 | PDS IS |
| Apollo Scientific Neat | GenX | 0.010 | 20.00 MeOH | 500 | 5.00 | 0.10 | 25.00 | PDS 2 |

Methanol (MeOH) is of LCMS grade. Table 3 shows an example of a preparation of working standards for GenX:

TABLE 3

Example of Preparation of Working Standards for GenX.

| WS Name | Volume of PDS/ICS Used [µL] | WS Final Volume [mL] | Solvent Used | WS Final Concentration [µg/L] |
|---|---|---|---|---|
| ICS 7/CCV HL | 100 of PDS | 10.00 | Preserved reagent water | 1.00 |
| ICS 1/CCV LL | 10.0 of ICS 7 | 1.00 | | 0.010 |
| ICS 2 | 25.0 of ICS 7 | 1.00 | | 0.025 |
| ICS 3 | 50.0 of ICS 7 | 1.00 | | 0.050 |
| ICS 4 | 100 of ICS 7 | 1.00 | | 0.10 |
| ICS 5/CCV ML | 250 of ICS 7 | 1.00 | | 0.25 |
| ICS 6 | 500 of ICS 7 | 1.00 | | 0.50 |
| MDL | 5.00 of ICS 7 | 1.00 | | 0.0050 |
| LFB ML (for DOC) | 250 of ICS 7 | 1.00 | | 0.25 |
| QCS | 25.0 of PDS 2 | 10.00 | | 0.25 |
| LFM/LFMD | 25.0 of PDS | 10.00 | Sample | 0.25 |

10.0 µL of IS is added to 1.00 mL of each WS resulting in concentration of 0.50 µg/L.

In this example, initial calibration standard 7 (ICS 7), the quality control sample (QCS), continuing calibration verification standards (CCV HL, ML and LL), and laboratory fortified matrix standards (LFB ML, LFM/LFMD) are prepared by adding determined volumes of primary dilution standard solutions to the stock blank or sample. Initial calibration standard 1 (ICS 1) through initial calibration standard 6 (ICS 6) are made by serial dilution of ICS 7 directly into a 2 mL vial. In various embodiments, the working standards are made fresh for every run. Initial calibration standard 7, the continuing calibration verification standards, the quality control sample and the method blank are typically transferred to 2 ml vials prior to analysis.

In step 110, the exact mass of the compounds (analytes/precursor ions) and their product ions is determined by high resolution mass spectroscopy.

In step 115, the settings are determined for gas flow and the temperature of the source of the mass spectrometer. Table 4 shows an example of settings determined for electrospray ionization (ESI) on an AGILENT 6495 mass spectrometer in step 115:

TABLE 4

Example of LC/MS/MS ESI Conditions developed for GenX.

ESI Conditions

| Polarity | Negative ion |
|---|---|
| Gas Temp (° C.) | 120 |
| Gas Flow (l/min) | 11 |
| Nebulizer (psi) | 20 |
| Sheath Gas Heater | 150 |
| Sheath Gas Flow | 6 |
| Capillary (V) | 3000 |
| V Charging | 0 |

Ion Funnel Parameters

| High Pressure RF | 90 |
|---|---|
| Low Pressure RF | 60 |

ESI is a technique used in mass spectrometry to produce ions using an electrospray in which a high voltage is applied to a liquid to create an aerosol that is ionized.

In Table 4, "Polarity" refers to an applied electrical field during ionization, which causes either positive or negative ions to be produced. "Gas Temp (° C.)" refers to a temperature in Celsius of an inert drying gas (typically nitrogen) that is used to promote the removal of solvent from aerosol particles in spray ionization. "Gas Flow (l/min)" refers to the volume per unit time (e.g. liters/minute or L/min) that the drying gas is dispersed. "Nebulizer (psi)" refers to the pressure (psi) utilized for the mass spectrometer nebulizer, which delivers a fine mist using the specified pressure. "Sheath Gas Heater" refers a temperature setting (° C.) for heating a sheath gas, which is an inert gas (typically nitrogen) introduced through a tube that is coaxial with the electrospray emitter to pneumatically assist the formation of the sprayed droplets. "Sheath Gas Flow" refers to the volume per unit time (e.g. liters/minute or L/min) that the sheath gas is dispersed. "Capillary (V)" refers to a voltage (in volts) applied to the tip of a metal capillary relative to the surrounding source-sampling cone or heated capillary. This strong electric field causes the dispersion of the sample solution into an aerosol of highly charged electrospray droplets. "V charging" refers to a setting for a charging electrode in the instrument, in this example the instrument is an AGILENT 6495 mass spectrometer. "Ion Funnel Parameters" refers to settings for an ion funnel, which is used to focus a beam of ions using a series of stacked ring electrodes with decreasing inner diameter. A combined radio frequency (RF) and fixed electrical potential is applied to the grids.

In various embodiments, ESI conditions include a gas temperature setting ("Gas Temp (° C.)") of approximately 120° C. to approximately 160° C. In some embodiments, ESI conditions include a gas temperature setting of approximately 120° C. to approximately 155° C. In some embodiments, ESI conditions include a gas temperature setting of approximately 120° C. to approximately 150° C. In some embodiments, ESI conditions include a gas temperature setting of approximately 120° C. to approximately 145° C. In some embodiments, ESI conditions include a gas temperature setting of approximately 120° C. to approximately 140° C. In some embodiments, ESI conditions include a gas temperature setting of approximately 120° C. to approximately 135° C. In some embodiments, ESI conditions include a gas temperature setting of approximately 120° C. to approximately 130° C. In some embodiments, ESI conditions include a gas temperature setting of approximately 120° C. to approximately 125° C.

In some embodiments, ESI conditions include a gas temperature setting of approximately 125° C. to approximately 160° C. In some embodiments, ESI conditions include a gas temperature setting of approximately 125° C. to approximately 155° C. In some embodiments, ESI conditions include a gas temperature setting of approximately 125° C. to approximately 150° C. In some embodiments, ESI conditions include a gas temperature setting of approximately 125° C. to approximately 145° C. In some embodiments, ESI conditions include a gas temperature setting of approximately 125° C. to approximately 140° C. In some embodiments, ESI conditions include a gas temperature setting of approximately 125° C. to approximately 135° C. In some embodiments, ESI conditions include a gas temperature setting of approximately 125° C. to approximately 130° C. In some embodiments, ESI conditions include a gas temperature setting of approximately 125° C.

In some embodiments, ESI conditions include a gas temperature setting of approximately 130° C. to approximately 160° C. In some embodiments, ESI conditions include a gas temperature setting of approximately 130° C. to approximately 155° C. In some embodiments, ESI conditions include a gas temperature setting of approximately 130° C. to approximately 150° C. In some embodiments, ESI conditions include a gas temperature setting of approximately 130° C. to approximately 145° C. In some embodiments, ESI conditions include a gas temperature setting of approximately 130° C. to approximately 140° C. In some embodiments, ESI conditions include a gas temperature setting of approximately 130° C. to approximately 135° C. In some embodiments, ESI conditions include a gas temperature setting of approximately 130° C.

In some embodiments, ESI conditions include a gas temperature setting of approximately 135° C. to approximately 160° C. In some embodiments, ESI conditions include a gas temperature setting of approximately 135° C. to approximately 155° C. In some embodiments, ESI conditions include a gas temperature setting of approximately 135° C. to approximately 150° C. In some embodiments, ESI conditions include a gas temperature setting of approximately 135° C. to approximately 145° C. In some embodiments, ESI conditions include a gas temperature setting of approximately 135° C. to approximately 140° C. In some embodiments, ESI conditions include a gas temperature setting of approximately 135° C.

In some embodiments, ESI conditions include a gas temperature setting of approximately 140° C. to approximately 160° C. In some embodiments, ESI conditions include a gas temperature setting of approximately 140° C. to approximately 155° C. In some embodiments, ESI conditions include a gas temperature setting of approximately 140° C. to approximately 150° C. In some embodiments, ESI conditions include a gas temperature setting of approximately 140° C. to approximately 145° C. In some embodiments, ESI conditions include a gas temperature setting of approximately 140° C.

In some embodiments, ESI conditions include a gas temperature setting of approximately 145° C. to approximately 160° C. In some embodiments, ESI conditions include a gas temperature setting of approximately 145° C. to approximately 155° C. In some embodiments, ESI conditions include a gas temperature setting of approximately 145° C. to approximately 150° C. In some embodiments, ESI conditions include a gas temperature setting of approximately 145° C.

In some embodiments, ESI conditions include a gas temperature setting of approximately 150° C. to approximately 160° C. In some embodiments, ESI conditions include a gas temperature setting of approximately 150° C. to approximately 155° C. In some embodiments, ESI conditions include a gas temperature setting of approximately 150° C.

In some embodiments, ESI conditions include a gas temperature setting of approximately 155° C. to approximately 160° C. In some embodiments, ESI conditions include a gas temperature setting of approximately 155° C. In some embodiments, ESI conditions include a gas temperature setting of approximately 160° C.

In exemplary embodiments, ESI conditions include a gas temperature setting of approximately 120° C.

In some embodiments, the ESI gas temperature setting is set on an AGILENT 6490 or 6495 mass spectrometer. In exemplary embodiments, the ESI gas temperature setting is set on an AGILENT 6495 mass spectrometer.

In various embodiments, ESI conditions include a sheath gas heater setting ("Sheath Gas Heater") of approximately 150° C. to approximately 275° C. In some embodiments, ESI conditions include a sheath gas heater setting of approximately 150° C. to approximately 270° C. In some embodiments, ESI conditions include a sheath gas heater setting of approximately 150° C. to approximately 265° C. In some embodiments, ESI conditions include a sheath gas heater setting of approximately 150° C. to approximately 260° C. In some embodiments, ESI conditions include a sheath gas heater setting of approximately 150° C. to approximately 255° C. In some embodiments, ESI conditions include a sheath gas heater setting of approximately 150° C. to approximately 250° C. In some embodiments, ESI conditions include a sheath gas heater setting of approximately 150° C. to approximately 245° C. In some embodiments, ESI conditions include a sheath gas heater setting of approximately 150° C. to approximately 240° C. In some embodiments, ESI conditions include a sheath gas heater setting of approximately 150° C. to approximately 235° C. In some embodiments, ESI conditions include a sheath gas heater setting of approximately 150° C. to approximately 230° C. In some embodiments, ESI conditions include a sheath gas heater setting of approximately 150° C. to approximately 225° C. In some embodiments, ESI conditions include a sheath gas heater setting of approximately 150° C. to approximately 220° C. In some embodiments, ESI conditions include a sheath gas heater setting of approximately 150° C. to approximately 215° C. In some embodiments, ESI conditions include a sheath gas heater setting of approximately 150° C. to approximately 210° C. In some embodiments, ESI conditions include a sheath gas heater setting of approximately 150° C. to approximately 205° C. In some embodiments, ESI conditions include a sheath gas heater setting of approximately 150° C. to approximately 200° C. In some embodiments, ESI conditions include a sheath gas heater setting of approximately 150° C. to approximately 195° C. In some embodiments, ESI conditions include a sheath gas heater setting of approximately 150° C. to approximately 190° C. In some embodiments, ESI conditions include a sheath gas heater setting of approximately 150° C. to approximately 185° C. In some embodiments, ESI conditions include a sheath gas heater setting of approximately 150° C. to approximately 180° C. In some embodiments, ESI conditions include a sheath gas heater setting of approximately 150° C. to approximately 175° C. In some embodiments, ESI conditions include a sheath gas heater setting of approximately 150° C. to approximately 170° C. In some embodiments, ESI conditions include a sheath gas heater setting of approximately 150° C. to approximately 165° C. In some embodiments, ESI conditions include a sheath gas heater setting of approximately 150° C. to approximately 160° C. In some embodiments, ESI conditions include a sheath gas heater setting of approximately 150° C. to approximately 155° C.

In some embodiments, ESI conditions include a sheath gas heater setting of approximately 155° C. to approximately 275° C. In some embodiments, ESI conditions include a sheath gas heater setting of approximately 155° C. to approximately 270° C. In some embodiments, ESI conditions include a sheath gas heater setting of approximately 155° C. to approximately 265° C. In some embodiments, ESI conditions include a sheath gas heater setting of approximately 155° C. to approximately 260° C. In some embodiments, ESI conditions include a sheath gas heater setting of approximately 155° C. to approximately 255° C. In some embodiments, ESI conditions include a sheath gas heater setting of approximately 155° C. to approximately 250° C. In some embodiments, ESI conditions include a sheath gas heater setting of approximately 155° C. to approximately 245° C. In some embodiments, ESI conditions include a sheath gas heater setting of approximately 155° C. to approximately 240° C. In some embodiments, ESI conditions include a sheath gas heater setting of approximately 155° C. to approximately 235° C. In some embodiments, ESI conditions include a sheath gas heater setting of approximately 155° C. to approximately 230° C. In some embodiments, ESI conditions include a sheath gas heater setting of approximately 155° C. to approximately 225° C. In some embodiments, ESI conditions include a sheath gas heater setting of approximately 155° C. to approximately 220° C. In some embodiments, ESI conditions include a sheath gas heater setting of approximately 155° C. to approximately 215° C. In some embodiments, ESI conditions include a sheath gas heater setting of approximately 155° C. to approximately 210° C. In some embodiments, ESI conditions include a sheath gas heater setting of approximately 155° C. to approximately 205° C. In some embodiments, ESI conditions include a sheath gas heater setting of approximately 155° C. to approximately 200° C. In some embodiments, ESI conditions include a sheath gas heater setting of approximately 155° C. to approximately 195° C. In some embodiments, ESI conditions include a sheath gas heater setting of approximately 155° C. to approximately 190° C. In some embodiments, ESI conditions include a sheath gas heater setting of approximately 155° C. to approximately 185° C. In some embodiments, ESI conditions include a sheath gas heater setting of approximately 155° C. to approximately 180° C. In some embodiments, ESI conditions include a sheath gas heater setting of approximately 155° C. to approximately 175° C. In some embodiments, ESI conditions include a sheath gas heater setting of approximately 155° C. to approximately 170° C. In some embodiments, ESI conditions include a sheath gas heater setting of approximately 155° C. to approximately 165° C. In some embodiments, ESI conditions include a sheath gas heater setting of approximately 155° C. to approximately 160° C. In some embodiments, ESI conditions include a sheath gas heater setting of approximately 155° C.

In some embodiments, ESI conditions include a sheath gas heater setting of approximately 160° C. to approximately 275° C. In some embodiments, ESI conditions include a sheath gas heater setting of approximately 160° C. to approximately 270° C. In some embodiments, ESI conditions include a sheath gas heater setting of approximately 160° C. to approximately 265° C. In some embodiments, ESI conditions include a sheath gas heater setting of approximately 160° C. to approximately 260° C. In some embodiments, ESI conditions include a sheath gas heater setting of approximately 160° C. to approximately 255° C. In some embodiments, ESI conditions include a sheath gas heater setting of approximately 160° C. to approximately 250° C. In some embodiments, ESI conditions include a sheath gas heater setting of approximately 160° C. to approximately 245° C. In some embodiments, ESI conditions include a sheath gas heater setting of approximately 160° C. to approximately 240° C. In some embodiments, ESI conditions include a sheath gas heater setting of approximately 160° C. to approximately 235° C. In some embodiments, ESI conditions include a sheath gas heater setting of approximately 160° C. to approximately 230° C. In some embodiments, ESI conditions include a sheath gas heater setting of approximately 160° C. to approximately 225° C. In some embodiments, ESI conditions include a sheath gas heater setting of approximately 160° C. to approximately 220° C. In some embodiments, ESI conditions include a sheath gas heater setting of approximately 160° C. to approximately 215° C. In some embodiments, ESI conditions include a sheath gas heater setting of approximately 160° C. to approximately 210° C. In some embodiments, ESI conditions include a sheath gas heater setting of approximately 160° C. to approximately 205° C. In some embodiments, ESI conditions include a sheath gas heater setting of approximately 160° C. to approximately 200° C. In some embodiments, ESI conditions include a sheath gas heater setting of approximately 160° C. to approximately 195° C. In some embodiments, ESI conditions include a sheath gas heater setting of approximately 160° C. to approximately 190° C. In some embodiments, ESI conditions include a sheath gas heater setting of approximately 160° C. to approximately 185° C. In some embodiments, ESI conditions include a sheath gas heater setting of approximately 160° C. to approximately 180° C. In some embodiments, ESI conditions include a sheath gas heater setting of approximately 160° C. to approximately 175° C. In some embodiments, ESI conditions include a sheath gas heater setting of approximately 160° C. to approximately 170° C. In some embodiments, ESI conditions include a sheath gas heater setting of approximately 160° C. to approximately 165° C. In some embodiments, ESI conditions include a sheath gas heater setting of approximately 160° C.

In some embodiments, ESI conditions include a sheath gas heater setting of approximately 165° C. to approximately 275° C. In some embodiments, ESI conditions include a sheath gas heater setting of approximately 165° C. to approximately 270° C. In some embodiments, ESI conditions include a sheath gas heater setting of approximately 165° C. to approximately 265° C. In some embodiments, ESI conditions include a sheath gas heater setting of approximately 165° C. to approximately 260° C. In some embodiments, ESI conditions include a sheath gas heater setting of approximately 165° C. to approximately 255° C. In some embodiments, ESI conditions include a sheath gas heater setting of approximately 165° C. to approximately 250° C. In some embodiments, ESI conditions include a sheath gas heater setting of approximately 165° C. to approximately 245° C. In some embodiments, ESI conditions include a sheath gas heater setting of approximately 165° C. to approximately 240° C. In some embodiments, ESI conditions include a sheath gas heater setting of approximately 165° C. to approximately 235° C. In some embodiments, ESI conditions include a sheath gas heater setting of approximately 165° C. to approximately 230° C. In some embodiments, ESI conditions include a sheath gas heater setting of approximately 165° C. to approximately 225° C. In some embodiments, ESI conditions include a sheath gas heater setting of approximately 165° C. to approximately 220° C. In some embodiments, ESI conditions include a sheath gas heater setting of approximately 165° C. to approximately 215° C. In some embodiments, ESI conditions include a sheath gas heater setting of approximately 165° C. to approximately 210° C. In some embodiments, ESI conditions include a sheath gas heater setting of approximately 165° C. to approximately 205° C. In some embodiments, ESI conditions include a sheath gas heater setting of approximately 165° C. to approximately 200° C. In some embodiments, ESI conditions include a sheath gas heater setting of approximately 165° C. to approximately 195° C. In some embodiments, ESI conditions include a sheath gas heater setting of approximately 165° C. to approximately 190° C. In some embodiments, ESI conditions include a sheath gas heater setting of approximately 165° C. to approximately 185° C. In some embodiments, ESI conditions include a sheath gas heater setting of approximately 165° C. to approximately 180° C. In some embodiments, ESI conditions include a sheath gas heater setting of approximately 165° C. to approximately 175° C. In some embodiments, ESI conditions include a sheath gas heater setting of approximately 165° C. to approximately 170° C. In some embodiments, ESI conditions include a sheath gas heater setting of approximately 165° C.

In some embodiments, ESI conditions include a sheath gas heater setting of approximately 170° C. to approximately 275° C. In some embodiments, ESI conditions include a sheath gas heater setting of approximately 170° C. to approximately 270° C. In some embodiments, ESI conditions include a sheath gas heater setting of approximately 170° C. to approximately 265° C. In some embodiments, ESI conditions include a sheath gas heater setting of approximately 170° C. to approximately 260° C. In some embodiments, ESI conditions include a sheath gas heater setting of approximately 170° C. to approximately 255° C. In some embodiments, ESI conditions include a sheath gas heater setting of approximately 170° C. to approximately 250° C. In some embodiments, ESI conditions include a sheath gas heater setting of approximately 170° C. to approximately 245° C. In some embodiments, ESI conditions include a sheath gas heater setting of approximately 170° C. to approximately 240° C. In some embodiments, ESI conditions include a sheath gas heater setting of approximately 170° C. to approximately 235° C. In some embodiments, ESI conditions include a sheath gas heater setting of approximately 170° C. to approximately 230° C. In some embodiments, ESI conditions include a sheath gas heater setting of approximately 170° C. to approximately 225° C. In some embodiments, ESI conditions include a sheath gas heater setting of approximately 170° C. to approximately 220° C. In some embodiments, ESI conditions include a sheath gas heater setting of approximately 170° C. to approximately 215° C. In some embodiments, ESI conditions include a sheath gas heater setting of approximately 170° C. to approximately 210° C. In some embodiments, ESI conditions include a sheath gas heater setting of approximately 170° C. to approximately 205° C. In some embodiments, ESI conditions include a sheath gas heater setting of approximately 170° C. to approximately 200° C. In some embodiments, ESI conditions include a sheath gas heater setting of approximately 170° C. to approximately 195° C. In some embodiments, ESI conditions include a sheath gas heater setting of approximately 170° C. to approximately 190° C. In some embodiments, ESI conditions include a sheath gas heater setting of approximately 170° C. to approximately 185° C. In some embodiments, ESI conditions include a sheath gas heater setting of approximately 170° C. to approximately 180° C. In some embodiments, ESI conditions include a sheath gas heater setting of approximately 170° C. to approximately 175° C. In some embodiments, ESI conditions include a sheath gas heater setting of approximately 170° C.

In some embodiments, ESI conditions include a sheath gas heater setting of approximately 175° C. to approximately 275° C. In some embodiments, ESI conditions include a sheath gas heater setting of approximately 175° C. to approximately 270° C. In some embodiments, ESI conditions include a sheath gas heater setting of approximately 175° C. to approximately 265° C. In some embodiments, ESI conditions include a sheath gas heater setting of approximately 175° C. to approximately 260° C. In some embodiments, ESI conditions include a sheath gas heater setting of approximately 175° C. to approximately 255° C. In some embodiments, ESI conditions include a sheath gas heater setting of approximately 175° C. to approximately 250° C. In some embodiments, ESI conditions include a sheath gas heater setting of approximately 175° C. to approximately 245° C. In some embodiments, ESI conditions include a sheath gas heater setting of approximately 175° C. to approximately 240° C. In some embodiments, ESI conditions include a sheath gas heater setting of approximately 175° C. to approximately 235° C. In some embodiments, ESI conditions include a sheath gas heater setting of approximately 175° C. to approximately 230° C. In some embodiments, ESI conditions include a sheath gas heater setting of approximately 175° C. to approximately 225° C. In some embodiments, ESI conditions include a sheath gas heater setting of approximately 175° C. to approximately 220° C. In some embodiments, ESI conditions include a sheath gas heater setting of approximately 175° C. to approximately 215° C. In some embodiments, ESI conditions include a sheath gas heater setting of approximately 175° C. to approximately 210° C. In some embodiments, ESI conditions include a sheath gas heater setting of approximately 175° C. to approximately 205° C. In some embodiments, ESI conditions include a sheath gas heater setting of approximately 175° C. to approximately 200° C. In some embodiments, ESI conditions include a sheath gas heater setting of approximately 175° C. to approximately 195° C. In some embodiments, ESI conditions include a sheath gas heater setting of approximately 175° C. to approximately 190° C. In some embodiments, ESI conditions include a sheath gas heater setting of approximately 175° C. to approximately 185° C. In some embodiments, ESI conditions include a sheath gas heater setting of approximately 175° C. to approximately 180° C. In some embodiments, ESI conditions include a sheath gas heater setting of approximately 175° C.

In some embodiments, ESI conditions include a sheath gas heater setting of approximately 180° C. to approximately 275° C. In some embodiments, ESI conditions include a sheath gas heater setting of approximately 180° C. to approximately 270° C. In some embodiments, ESI conditions include a sheath gas heater setting of approximately 180° C. to approximately 265° C. In some embodiments, ESI conditions include a sheath gas heater setting of approximately 180° C. to approximately 260° C. In some embodiments, ESI conditions include a sheath gas heater setting of approximately 180° C. to approximately 255° C. In some embodiments, ESI conditions include a sheath gas heater setting of approximately 180° C. to approximately 250° C. In some embodiments, ESI conditions include a sheath gas heater setting of approximately 180° C. to approximately 245° C. In some embodiments, ESI conditions include a sheath gas heater setting of approximately 180° C. to approximately 240° C. In some embodiments, ESI conditions include a sheath gas heater setting of approximately 180° C. to approximately 235° C. In some embodiments, ESI conditions include a sheath gas heater setting of approximately 180° C. to approximately 230° C. In some embodiments, ESI conditions include a sheath gas heater setting of approximately 180° C. to approximately 225° C. In some embodiments, ESI conditions include a sheath gas heater setting of approximately 180° C. to approximately 220° C. In some embodiments, ESI conditions include a sheath gas heater setting of approximately 180° C. to approximately 215° C. In some embodiments, ESI conditions include a sheath gas heater setting of approximately 180° C. to approximately 210° C. In some embodiments, ESI conditions include a sheath gas heater setting of approximately 180° C. to approximately 205° C. In some embodiments, ESI conditions include a sheath gas heater setting of approximately 180° C. to approximately 200° C. In some embodiments, ESI conditions include a sheath gas heater setting of approximately 180° C. to approximately 195° C. In some embodiments, ESI conditions include a sheath gas heater setting of approximately 180° C. to approximately 190° C. In some embodiments, ESI conditions include a sheath gas heater setting of approximately 180° C. to approximately 185° C. In some embodiments, ESI conditions include a sheath gas heater setting of approximately 180° C.

In some embodiments, ESI conditions include a sheath gas heater setting of approximately 185° C. to approximately 275° C. In some embodiments, ESI conditions include a sheath gas heater setting of approximately 185° C. to approximately 270° C. In some embodiments, ESI conditions include a sheath gas heater setting of approximately 185° C. to approximately 265° C. In some embodiments, ESI conditions include a sheath gas heater setting of approximately 185° C. to approximately 260° C. In some embodiments, ESI conditions include a sheath gas heater setting of approximately 185° C. to approximately 255° C. In some embodiments, ESI conditions include a sheath gas heater setting of approximately 185° C. to approximately 250° C. In some embodiments, ESI conditions include a sheath gas heater setting of approximately 185° C. to approximately 245° C. In some embodiments, ESI conditions include a sheath gas heater setting of approximately 185° C. to approximately 240° C. In some embodiments, ESI conditions include a sheath gas heater setting of approximately 185° C. to approximately 235° C. In some embodiments, ESI conditions include a sheath gas heater setting of approximately 185° C. to approximately 230° C. In some embodiments, ESI conditions include a sheath gas heater setting of approximately 185° C. to approximately 225° C. In some embodiments, ESI conditions include a sheath gas heater setting of approximately 185° C. to approximately 220° C. In some embodiments, ESI conditions include a sheath gas heater setting of approximately 185° C. to approximately 215° C. In some embodiments, ESI conditions include a sheath gas heater setting of approximately 185° C. to approximately 210° C. In some embodiments, ESI conditions include a sheath gas heater setting of approximately 185° C. to approximately 205° C. In some embodiments, ESI conditions include a sheath gas heater setting of approximately 185° C. to approximately 200° C. In some embodiments, ESI conditions include a sheath gas heater setting of approximately 185° C. to approximately 195° C. In some embodiments, ESI conditions include a sheath gas heater setting of approximately 185° C. to approximately 190° C. In some embodiments, ESI conditions include a sheath gas heater setting of approximately 185° C.

In some embodiments, ESI conditions include a sheath gas heater setting of approximately 190° C. to approximately 275° C. In some embodiments, ESI conditions include a sheath gas heater setting of approximately 190° C. to approximately 270° C. In some embodiments, ESI conditions include a sheath gas heater setting of approximately 190° C. to approximately 265° C. In some embodiments, ESI conditions include a sheath gas heater setting of approximately 190° C. to approximately 260° C. In some embodiments, ESI conditions include a sheath gas heater setting of approximately 190° C. to approximately 255° C. In some embodiments, ESI conditions include a sheath gas heater setting of approximately 190° C. to approximately 250° C. In some embodiments, ESI conditions include a sheath gas heater setting of approximately 190° C. to approximately 245° C. In some embodiments, ESI conditions include a sheath gas heater setting of approximately 190° C. to approximately 240° C. In some embodiments, ESI conditions include a sheath gas heater setting of approximately 190° C. to approximately 235° C. In some embodiments, ESI conditions include a sheath gas heater setting of approximately 190° C. to approximately 230° C. In some embodiments, ESI conditions include a sheath gas heater setting of approximately 190° C. to approximately 225° C. In some embodiments, ESI conditions include a sheath gas heater setting of approximately 190° C. to approximately 220° C. In some embodiments, ESI conditions include a sheath gas heater setting of approximately 190° C. to approximately 215° C. In some embodiments, ESI conditions include a sheath gas heater setting of approximately 190° C. to approximately 210° C. In some embodiments, ESI conditions include a sheath gas heater setting of approximately 190° C. to approximately 205° C. In some embodiments, ESI conditions include a sheath gas heater setting of approximately 190° C. to approximately 200° C. In some embodiments, ESI conditions include a sheath gas heater setting of approximately 190° C. to approximately 195° C. In some embodiments, ESI conditions include a sheath gas heater setting of approximately 190° C.

In some embodiments, ESI conditions include a sheath gas heater setting of approximately 195° C. to approximately 275° C. In some embodiments, ESI conditions include a sheath gas heater setting of approximately 195° C. to approximately 270° C. In some embodiments, ESI conditions include a sheath gas heater setting of approximately 195° C. to approximately 265° C. In some embodiments, ESI conditions include a sheath gas heater setting of approximately 195° C. to approximately 260° C. In some embodiments, ESI conditions include a sheath gas heater setting of approximately 195° C. to approximately 255° C. In some embodiments, ESI conditions include a sheath gas heater setting of approximately 195° C. to approximately 250° C. In some embodiments, ESI conditions include a sheath gas heater setting of approximately 195° C. to approximately 245° C. In some embodiments, ESI conditions include a sheath gas heater setting of approximately 195° C. to approximately 240° C. In some embodiments, ESI conditions include a sheath gas heater setting of approximately 195° C. to approximately 235° C. In some embodiments, ESI conditions include a sheath gas heater setting of approximately 195° C. to approximately 230° C. In some embodiments, ESI conditions include a sheath gas heater setting of approximately 195° C. to approximately 225° C. In some embodiments, ESI conditions include a sheath gas heater setting of approximately 195° C. to approximately 220° C. In some embodiments, ESI conditions include a sheath gas heater setting of approximately 195° C. to approximately 215° C. In some embodiments, ESI conditions include a sheath gas heater setting of approximately 195° C. to approximately 210° C. In some embodiments, ESI conditions include a sheath gas heater setting of approximately 195° C. to approximately 205° C. In some embodiments, ESI conditions include a sheath gas heater setting of approximately 195° C. to approximately 200° C. In some embodiments, ESI conditions include a sheath gas heater setting of approximately 195° C.

In some embodiments, ESI conditions include a sheath gas heater setting of approximately 200° C. to approximately 275° C. In some embodiments, ESI conditions include a sheath gas heater setting of approximately 200° C. to approximately 270° C. In some embodiments, ESI conditions include a sheath gas heater setting of approximately 200° C. to approximately 265° C. In some embodiments, ESI conditions include a sheath gas heater setting of approximately 200° C. to approximately 260° C. In some embodiments, ESI conditions include a sheath gas heater setting of approximately 200° C. to approximately 255° C. In some embodiments, ESI conditions include a sheath gas heater setting of approximately 200° C. to approximately 250° C. In some embodiments, ESI conditions include a sheath gas heater setting of approximately 200° C. to approximately 245° C. In some embodiments, ESI conditions include a sheath gas heater setting of approximately 200° C. to approximately 240° C. In some embodiments, ESI conditions include a sheath gas heater setting of approximately 200° C. to approximately 235° C. In some embodiments, ESI conditions include a sheath gas heater setting of approximately 200° C. to approximately 230° C. In some embodiments, ESI conditions include a sheath gas heater setting of approximately 200° C. to approximately 225° C. In some embodiments, ESI conditions include a sheath gas heater setting of approximately 200° C. to approximately 220° C. In some embodiments, ESI conditions include a sheath gas heater setting of approximately 200° C. to approximately 215° C. In some embodiments, ESI conditions include a sheath gas heater setting of approximately 200° C. to approximately 210° C. In some embodiments, ESI conditions include a sheath gas heater setting of approximately 200° C. to approximately 205° C. In some embodiments, ESI conditions include a sheath gas heater setting of approximately 200° C.

In some embodiments, ESI conditions include a sheath gas heater setting of approximately 205° C. to approximately 275° C. In some embodiments, ESI conditions include a sheath gas heater setting of approximately 205° C. to approximately 270° C. In some embodiments, ESI conditions include a sheath gas heater setting of approximately 205° C. to approximately 265° C. In some embodiments, ESI conditions include a sheath gas heater setting of approximately 205° C. to approximately 260° C. In some embodiments, ESI conditions include a sheath gas heater setting of approximately 205° C. to approximately 255° C. In some embodiments, ESI conditions include a sheath gas heater setting of approximately 205° C. to approximately 250° C. In some embodiments, ESI conditions include a sheath gas heater setting of approximately 205° C. to approximately 245° C. In some embodiments, ESI conditions include a sheath gas heater setting of approximately 205° C. to approximately 240° C. In some embodiments, ESI conditions include a sheath gas heater setting of approximately 205° C. to approximately 235° C. In some embodiments, ESI conditions include a sheath gas heater setting of approximately 205° C. to approximately 230° C. In some embodiments, ESI conditions include a sheath gas heater setting of approximately 205° C. to approximately 225° C. In some embodiments, ESI conditions include a sheath gas heater setting of approximately 205° C. to approximately 220° C. In some embodiments, ESI conditions include a sheath gas heater setting of approximately 205° C. to approximately 215° C. In some embodiments, ESI conditions include a sheath gas heater setting of approximately 205° C. to approximately 210° C. In some embodiments, ESI conditions include a sheath gas heater setting of approximately 205° C.

In some embodiments, ESI conditions include a sheath gas heater setting of approximately 210° C. to approximately 275° C. In some embodiments, ESI conditions include a sheath gas heater setting of approximately 210° C. to approximately 270° C. In some embodiments, ESI conditions include a sheath gas heater setting of approximately 210° C. to approximately 265° C. In some embodiments, ESI conditions include a sheath gas heater setting of approximately 210° C. to approximately 260° C. In some embodiments, ESI conditions include a sheath gas heater setting of approximately 210° C. to approximately 255° C. In some embodiments, ESI conditions include a sheath gas heater setting of approximately 210° C. to approximately 250° C. In some embodiments, ESI conditions include a sheath gas heater setting of approximately 210° C. to approximately 245° C. In some embodiments, ESI conditions include a sheath gas heater setting of approximately 210° C. to approximately 240° C. In some embodiments, ESI conditions include a sheath gas heater setting of approximately 210° C. to approximately 235° C. In some embodiments, ESI conditions include a sheath gas heater setting of approximately 210° C. to approximately 230° C. In some embodiments, ESI conditions include a sheath gas heater setting of approximately 210° C. to approximately 225° C. In some embodiments, ESI conditions include a sheath gas heater setting of approximately 210° C. to approximately 220° C. In some embodiments, ESI conditions include a sheath gas heater setting of approximately 210° C. to approximately 215° C. In some embodiments, ESI conditions include a sheath gas heater setting of approximately 210° C.

In some embodiments, ESI conditions include a sheath gas heater setting of approximately 215° C. to approximately 275° C. In some embodiments, ESI conditions include a sheath gas heater setting of approximately 215° C. to approximately 270° C. In some embodiments, ESI conditions include a sheath gas heater setting of approximately 215° C. to approximately 265° C. In some embodiments, ESI conditions include a sheath gas heater setting of approximately 215° C. to approximately 260° C. In some embodiments, ESI conditions include a sheath gas heater setting of approximately 215° C. to approximately 255° C. In some embodiments, ESI conditions include a sheath gas heater setting of approximately 215° C. to approximately 250° C. In some embodiments, ESI conditions include a sheath gas heater setting of approximately 215° C. to approximately 245° C. In some embodiments, ESI conditions include a sheath gas heater setting of approximately 215° C. to approximately 240° C. In some embodiments, ESI conditions include a sheath gas heater setting of approximately 215° C. to approximately 235° C. In some embodiments, ESI conditions include a sheath gas heater setting of approximately 215° C. to approximately 230° C. In some embodiments, ESI conditions include a sheath gas heater setting of approximately 215° C. to approximately 225° C. In some embodiments, ESI conditions include a sheath gas heater setting of approximately 215° C. to approximately 220° C. In some embodiments, ESI conditions include a sheath gas heater setting of approximately 215° C.

In some embodiments, ESI conditions include a sheath gas heater setting of approximately 220° C. to approximately 275° C. In some embodiments, ESI conditions include a sheath gas heater setting of approximately 220° C. to approximately 270° C. In some embodiments, ESI conditions include a sheath gas heater setting of approximately 220° C. to approximately 265° C. In some embodiments, ESI conditions include a sheath gas heater setting of approximately 220° C. to approximately 260° C. In some embodiments, ESI conditions include a sheath gas heater setting of approximately 220° C. to approximately 255° C. In some embodiments, ESI conditions include a sheath gas heater setting of approximately 220° C. to approximately 250° C. In some embodiments, ESI conditions include a sheath gas heater setting of approximately 220° C. to approximately 245° C. In some embodiments, ESI conditions include a sheath gas heater setting of approximately 220° C. to approximately 240° C. In some embodiments, ESI conditions include a sheath gas heater setting of approximately 220° C. to approximately 235° C. In some embodiments, ESI conditions include a sheath gas heater setting of approximately 220° C. to approximately 230° C. In some embodiments, ESI conditions include a sheath gas heater setting of approximately 220° C. to approximately 225° C. In some embodiments, ESI conditions include a sheath gas heater setting of approximately 220° C.

In some embodiments, ESI conditions include a sheath gas heater setting of approximately 225° C. to approximately 275° C. In some embodiments, ESI conditions include a sheath gas heater setting of approximately 225° C. to approximately 270° C. In some embodiments, ESI conditions include a sheath gas heater setting of approximately 225° C. to approximately 265° C. In some embodiments, ESI conditions include a sheath gas heater setting of approximately 225° C. to approximately 260° C. In some embodiments, ESI conditions include a sheath gas heater setting of approximately 225° C. to approximately 255° C. In some embodiments, ESI conditions include a sheath gas heater setting of approximately 225° C. to approximately 250° C. In some embodiments, ESI conditions include a sheath gas heater setting of approximately 225° C. to approximately 245° C. In some embodiments, ESI conditions include a sheath gas heater setting of approximately 225° C. to approximately 240° C. In some embodiments, ESI conditions include a sheath gas heater setting of approximately 225° C. to approximately 235° C. In some embodiments, ESI conditions include a sheath gas heater setting of approximately 225° C. to approximately 230° C. In some embodiments, ESI conditions include a sheath gas heater setting of approximately 225° C.

In some embodiments, ESI conditions include a sheath gas heater setting of approximately 230° C. to approximately 275° C. In some embodiments, ESI conditions include a sheath gas heater setting of approximately 230° C. to approximately 270° C. In some embodiments, ESI conditions include a sheath gas heater setting of approximately 230° C. to approximately 265° C. In some embodiments, ESI conditions include a sheath gas heater setting of approximately 230° C. to approximately 260° C. In some embodiments, ESI conditions include a sheath gas heater setting of approximately 230° C. to approximately 255° C. In some embodiments, ESI conditions include a sheath gas heater setting of approximately 230° C. to approximately 250° C. In some embodiments, ESI conditions include a sheath gas heater setting of approximately 230° C. to approximately 245° C. In some embodiments, ESI conditions include a sheath gas heater setting of approximately 230° C. to approximately 240° C. In some embodiments, ESI conditions include a sheath gas heater setting of approximately 230° C. to approximately 235° C. In some embodiments, ESI conditions include a sheath gas heater setting of approximately 230° C.

In some embodiments, ESI conditions include a sheath gas heater setting of approximately 235° C. to approximately 275° C. In some embodiments, ESI conditions include a sheath gas heater setting of approximately 235° C. to approximately 270° C. In some embodiments, ESI conditions include a sheath gas heater setting of approximately 235° C. to approximately 265° C. In some embodiments, ESI conditions include a sheath gas heater setting of approximately 235° C. to approximately 260° C. In some embodiments, ESI conditions include a sheath gas heater setting of approximately 235° C. to approximately 255° C. In some embodiments, ESI conditions include a sheath gas heater setting of approximately 235° C. to approximately 250° C. In some embodiments, ESI conditions include a sheath gas heater setting of approximately 235° C. to approximately 245° C. In some embodiments, ESI conditions include a sheath gas heater setting of approximately 235° C. to approximately 240° C. In some embodiments, ESI conditions include a sheath gas heater setting of approximately 235° C.

In some embodiments, ESI conditions include a sheath gas heater setting of approximately 240° C. to approximately 275° C. In some embodiments, ESI conditions include a sheath gas heater setting of approximately 240° C. to approximately 270° C. In some embodiments, ESI conditions include a sheath gas heater setting of approximately 240° C. to approximately 265° C. In some embodiments, ESI conditions include a sheath gas heater setting of approximately 240° C. to approximately 260° C. In some embodiments, ESI conditions include a sheath gas heater setting of approximately 240° C. to approximately 255° C. In some embodiments, ESI conditions include a sheath gas heater setting of approximately 240° C. to approximately 250° C. In some embodiments, ESI conditions include a sheath gas heater setting of approximately 240° C. to approximately 245° C. In some embodiments, ESI conditions include a sheath gas heater setting of approximately 240° C.

In some embodiments, ESI conditions include a sheath gas heater setting of approximately 245° C. to approximately 275° C. In some embodiments, ESI conditions include a sheath gas heater setting of approximately 245° C. to approximately 270° C. In some embodiments, ESI conditions include a sheath gas heater setting of approximately 245° C. to approximately 265° C. In some embodiments, ESI conditions include a sheath gas heater setting of approximately 245° C. to approximately 260° C. In some embodiments, ESI conditions include a sheath gas heater setting of approximately 245° C. to approximately 255° C. In some embodiments, ESI conditions include a sheath gas heater setting of approximately 245° C. to approximately 250° C. In some embodiments, ESI conditions include a sheath gas heater setting of approximately 245° C.

In some embodiments, ESI conditions include a sheath gas heater setting of approximately 250° C. to approximately 275° C. In some embodiments, ESI conditions include a sheath gas heater setting of approximately 250° C. to approximately 270° C. In some embodiments, ESI conditions include a sheath gas heater setting of approximately 250° C. to approximately 265° C. In some embodiments, ESI conditions include a sheath gas heater setting of approximately 250° C. to approximately 260° C. In some embodiments, ESI conditions include a sheath gas heater setting of approximately 250° C. to approximately 255° C. In some embodiments, ESI conditions include a sheath gas heater setting of approximately 250° C.

In some embodiments, ESI conditions include a sheath gas heater setting of approximately 255° C. to approximately 275° C. In some embodiments, ESI conditions include a sheath gas heater setting of approximately 255° C. to approximately 270° C. In some embodiments, ESI conditions include a sheath gas heater setting of approximately 255° C. to approximately 265° C. In some embodiments, ESI conditions include a sheath gas heater setting of approximately 255° C. to approximately 260° C. In some embodiments, ESI conditions include a sheath gas heater setting of approximately 255° C.

In some embodiments, ESI conditions include a sheath gas heater setting of approximately 260° C. to approximately 275° C. In some embodiments, ESI conditions include a sheath gas heater setting of approximately 260° C. to approximately 270° C. In some embodiments, ESI conditions include a sheath gas heater setting of approximately 260° C. to approximately 265° C. In some embodiments, ESI conditions include a sheath gas heater setting of approximately 260° C.

In some embodiments, ESI conditions include a sheath gas heater setting of approximately 265° C. to approximately 275° C. In some embodiments, ESI conditions include a sheath gas heater setting of approximately 265° C. to approximately 270° C. In some embodiments, ESI conditions include a sheath gas heater setting of approximately 265° C.

In some embodiments, ESI conditions include a sheath gas heater setting of approximately 270° C. to approximately 275° C. In some embodiments, ESI conditions include a sheath gas heater setting of approximately 270° C. In some embodiments, ESI conditions include a sheath gas heater setting of approximately 275° C.

In exemplary embodiments, ESI conditions include a sheath gas heater setting of approximately 150° C.

In some embodiments, the ESI sheath gas heater setting is set on an AGILENT 6490 or 6495 mass spectrometer. In exemplary embodiments, the ESI sheath gas heater setting is set on an AGILENT 6495 mass spectrometer.

In various embodiments, ESI conditions include a sheath gas flow ("Sheath Gas Flow") of approximately 6 L/min to approximately 11 L/min. In some embodiments, ESI conditions include a sheath gas flow of approximately 6 L/min to approximately 10 L/min. In some embodiments, ESI conditions include a sheath gas flow of approximately 6 L/min to approximately 9 L/min. In some embodiments, ESI conditions include a sheath gas flow of approximately 6 L/min to approximately 8 L/min. In some embodiments, ESI conditions include a sheath gas flow of approximately 6 L/min to approximately 7 L/min.

In some embodiments, ESI conditions include a sheath gas flow of approximately 7 L/min to approximately 11 L/min. In some embodiments, ESI conditions include a sheath gas flow of approximately 7 L/min to approximately 10 L/min. In some embodiments, ESI conditions include a sheath gas flow of approximately 7 L/min to approximately 9 L/min. In some embodiments, ESI conditions include a sheath gas flow of approximately 7 L/min to approximately 8 L/min. In some embodiments, ESI conditions include a sheath gas flow of approximately 7 L/min.

In some embodiments, ESI conditions include a sheath gas flow of approximately 8 L/min to approximately 11 L/min. In some embodiments, ESI conditions include a sheath gas flow of approximately 8 L/min to approximately 10 L/min. In some embodiments, ESI conditions include a sheath gas flow of approximately 8 L/min to approximately 9 L/min. In some embodiments, ESI conditions include a sheath gas flow of approximately 8 L/min.

In some embodiments, ESI conditions include a sheath gas flow of approximately 9 L/min to approximately 11 L/min. In some embodiments, ESI conditions include a sheath gas flow of approximately 9 L/min to approximately 10 L/min. In some embodiments, ESI conditions include a sheath gas flow of approximately 9 L/min.

In some embodiments, ESI conditions include a sheath gas flow of approximately 10 L/min to approximately 11 L/min. In some embodiments, ESI conditions include a sheath gas flow of approximately 10 L/min. In some embodiments, ESI conditions include a sheath gas flow of approximately 11 L/min.

In exemplary embodiments, ESI conditions include a sheath gas flow of approximately 6 L/min.

In some embodiments, the ESI sheath gas flow setting is set on an AGILENT 6490 or 6495 mass spectrometer. In exemplary embodiments, the ESI sheath gas flow setting is set on an AGILENT 6495 mass spectrometer.

In step 120, aqueous standards as described supra are prepared for the determination of chromatographic conditions.

In step 125, a chromatographic gradient is developed for the compounds (analytes). In one embodiment of a developed chromatographic gradient, the column used is an analytical column: ZORBAX ECLIPSE PLUS C18, 2.1×50 mm, 1.8 um. The following conditions with the column were used: Column temperature=40° C.; injection volume=75 μL; and flow=0.30 mL/min. Table 5 shows an example of a developed GenX gradient method on this column under these parameters:

TABLE 5

Example of an LC Gradient for GenX.
LC Gradient Program-Negative Ions

| Time (min) | % 5 mM ammonium acetate | % Methanol |
| --- | --- | --- |
| 0 | 95 | 5 |
| 1 | 5 | 95 |
| 2 | 5 | 95 |
| 2.2 | 95 | 5 |
| 3.2 | 95 | 5 |

In step 130 the chromatographic gradient developed in step 125 is combined with the mass spectroscopy settings determined in step 115. Table 6 shows an example of triple quadrapole MS/MS method conditions for GenX after combination with the Table 5 LC gradient:

TABLE 6

Example of LC/MS/MS Method Conditions for GenX.
Triple Quadrupole MS/MS Method Conditions

| Analyte | Scan Type | Retention Time (min) | Precursor Ion (m/z) | Product Ion (m/z)[a] | MS1 MS2 | Frag Voltage | Collision Energy (ev)[b] | Cell Acceleration (V) |
| --- | --- | --- | --- | --- | --- | --- | --- | --- |
| GenX | Primary | 2.44 | 329 | 168.9 | Unit | 380 | 5 | 1 |
| GenX | Qualifier | 2.44 | 329 | 285 | Unit | 380 | 1 | 1 |
| GenX-C13 | Primary | 2.44 | 332 | 287 | Unit | 380 | 1 | 1 |

[a]Ions used for quantitation purposes.
[b]Nitrogen used as collision gas

For Table 6, the precursor ion is the deprotonated molecule ([M–H]$^-$) of the target analyte. In MS/MS, the precursor ion is mass selected and fragmented by collisionally activated dissociation to produce distinctive product ions of smaller m/z. The product ion is one of the fragment ions produced in MS/MS by the collisionally activated dissociation of the precursor ion. In this example, the GenX primary ion is 168.9 and the GenX qualifier ion is 285. However, either ion can be used for primary and qualifier ions, i.e., the GenX primary ion may be 285 and the GenX qualifier ion may be 168.9.

In the examples shown in Tables 4-6 the following instrumentation is used:
  i) AGILENT LC/MS/MS System (Column: Analytical column ZORBAX ECLIPSE PLUS C18, 2.1×50 mm, 1.8 um);
  ii) AGILENT 1290 INFINITY Autosampler;
  iii) AGILENT 1290 Binary Pump;
  iv) AGILENT 1290 TCC Column Compartment; and
  v) AGILENT 6495 Mass Spectrometer.

In the examples shown in Tables 4-6 the data software used is AGILENT MASS HUNTER.

In steps 135 and 140, a practical range of detection is determined using calibration standards prepared as described supra and method validation samples. In these steps, quality control (QC) includes a demonstration of capability (DOC) requirement and a determination of the method detection limit (MDL). Ongoing QC requirements are continuously met when preparing and analyzing samples.

In various embodiments, an initial demonstration of capability (IDC) is performed prior to analyzing any field samples and any time major method modifications are made. The following steps are exemplary:

i) Generate an acceptable instrument calibration and demonstrate a low system background by analyzing an acceptable method blank. The mass spectrometer is calibrated according to the manufacturer's recommendations. Prior to the analysis of samples, the instrument's performance is optimized, and an instrument calibration curve is generated. The instrument is calibrated using standards at seven (i.e., ICS1-ICS7) concentrations, as listed in Table 3. They are analyzed with every analytical run. ICS1 contains the analyte at a concentration equal to or below the minimum reporting level (MRL). A calibration curve is generated for each analyte by plotting the responses against known concentrations. In preferred embodiments, linear and quadratic regression models are used. Both weighted and unweighted models are used. In various embodiments, a calibration curve regression model and a range of calibration levels is used for all routine sample analysis. The initial calibration is verified by analyzing various concentrations of CCV ((low level) LL, (medium level) ML, (high level) HL) prior to sample analysis and after every 10 samples (see Table 11 below).

ii) Analyze a method blank to demonstrate low background contamination (an example of method blank (MB) acceptance criteria is shown in Table 11 below).

iii) Demonstrate method precision and accuracy by analyzing 4 replicates of a laboratory fortified method blank medium level (LFBML) prepared as indicated in Table 3 and as described supra. The acceptance criteria are as follows: relative percent difference (RPD) <20% and accuracy as mean percent recovery is within ±30%.

iv) Establish the method detection limit (MDL) by analyzing seven replicates of laboratory fortified blank (LFB) fortified at less than or equal to the concentration of the reporting limits (RL) listed in Table 10. In some embodiments, the MDL study is performed over a minimum of 3 days. The determination of the MDL is described in more detail infra.

v) The MDL verification is performed at the time of initial method development, each time the MDL study is performed, and on an annual basis. The LFB at a concentration of 2-3 times the calculated MDL value (but less than RL and concentration used for MDL study and less than or equal to the required detection levels (RDL) if applicable) is prepared and analyzed. The analyte must be positively identified. If an analyte identification cannot be confirmed at the prepared concentration the instrument shall be maintained to restore sensitivity or the RL of this analyte must be re-evaluated.

Ongoing quality control applied when performing this method includes analyzing acceptable instrument calibration/calibration verification standards, MB, QCS, LFM, and LFMD with tested samples at the frequency and acceptance criteria required.

Table 11 (infra) illustrates an example of a laboratory analytical run sequence for this method, with QC parameters frequency, concentrations and acceptance criteria.

An example of a DOC Study including the demonstration of laboratory precision and accuracy are presented in Table 7 using 75 µL injection volumes:

TABLE 7

Example of a DOC Study for GenX.

| Data File | 17 | 18 | 19 | 20 | | Accuracy | Method's | | Precision | Method's |
|---|---|---|---|---|---|---|---|---|---|---|
| | Amount | Amount Recovered | | | | as Mean | Accuracy | Standard | | Precision |
| Analyte Name | Added [µg/L] | LFB** [µg/L] | LFB** [µg/L] | LFB** [µg/L] | LFB** [µg/L] | Mean [µg/L] | Recovery [%] | Limits [%] | Deviation [µg/L] | as RSD* [%] | Limits [%] |
| GenX | 0.250 | 0.2532 | 0.2532 | 0.2571 | 0.2536 | 0.254 | 101.7 | 70.0-130.0 | 0.0019 | 0.7 | <20.0 |

Determination of MDL

MDL (Method Detection Limits) are the minimum concentration of a substance that can be reported with 99% confidence that the measured concentration is distinguishable from Method Blank results. An example of a procedure for determining MDL is as follows:

First, an estimate is made of an initial MDL using one or more of: i) a mean determined concentration plus three times the standard deviation of a set of MB; ii) a concentration value that corresponds to an instrument signal/noise in the range of 3 to 5; iii) a concentration equivalent of three times the standard deviation of replicate instrumental measurements of spiked blanks; iv) a region of the calibration where there is a significant change in sensitivity, such as a break in the slope of the calibration; v) an instrumental limitation; and vi) a previously determined MDL.

Second, an initial MDL determination is made by selecting a spiking level, typically 2-10 times the estimated method detection limit from above, but less than the value of the laboratory established RL and less than or equal to a regulatory authority reported required detection limit (RDL), if one exists. Once the spiking level is determined, a minimum of seven laboratory standards in reagent water (containing all method preservatives, if applicable) are made at the selected spiking level concentration and they are processed through all steps of the method. Generally, the standards used for the MDL are prepared in at least three batches on three separate calendar dates and analyzed on three separate calendar dates. Preparation and analysis may be performed on the same day. In general, statistical outlier removal procedures are not used to remove data for the initial MDL determination since the total number of observations is small and the purpose of the MDL procedure is to capture routine method variability. However, documented instances of gross failures (e.g., instrument malfunctions, mislabeled samples, cracked vials) may be excluded from the calculations, provided that at least seven spiked samples and seven method blanks are available. After the method is run, the spiking level is evaluated. If any result for any individual analyte from the spiked samples does not meet a qualitative method identification criterion or does not provide a numerical result greater than zero, then the method is repeated with spiked samples at a higher concentration.

The method MDL is the greater of either an MDL based on spiked samples (MDLs) or an MDL based on method blanks (MDLb).

The MDLs is calculated as shown below:

First, a mean of the measured concentration values X is calculated as shown below:

$$X = \sum \frac{Xi}{n}$$

Where:
    i=from 1 to n;
    n=the number of data points; and
    Xi=the measured concentration value of an individual laboratory standard.

Second, a mean percent recovery (R) is calculated as shown below:

$$R = \frac{X}{T} \times 100\%$$

Where:
    X=mean of the measured concentration values; and
    T=true concentration used.

Third, a standard deviation (Ss) is calculated as shown below:

$$Ss = \sqrt{\frac{\sum (Xi - X)^2}{n - 1}}$$

Where:
    i=from 1 to n
    n=the number of data points;
    Xi=the measured concentration value of an individual laboratory standard; and
    X=mean of the measured concentration values.

The MDLs is then calculated as shown below:

$$MDLs = t_{(n-1,\ 1-\alpha=0.99)} * Ss$$

Where:
    $t_{(n-1,\ 1-\alpha=0.99)}$=the Student's t-value appropriate for a single-tailed $99^{th}$ percentile t statistic and a standard deviation estimate with n-1 degrees of freedom (see Table 8 below); and
    Ss=standard deviation of the replicate spiked sample analyses.

For the MLDb, one of the following criterion is applied:
i) If none of the method blanks give numerical results for an individual analyte, the MDLb does not apply and the MDLs is used. A numerical result includes both positive and negative results, including results below a current MDL, but not results of "ND" (not detected) commonly observed when a peak is not present in chromatographic analysis;
ii) If some (but not all) of the method blanks for an individual analyte give numerical results, set the MDLb equal to the highest method blank result; or
iii) If all of the method blanks for an individual analyte give numerical results, then the MDLb is calculated as shown below:

First, a mean of the measured concentration values X is calculated as shown below:

$$X = \sum \frac{Xi}{n}$$

Where:
    i=from 1 to n;
    n=the number of data points; and
    Xi=the measured concentration value of an individual MB.

Second, a standard deviation (Sb) is calculated as shown below:

$$Sb = \sqrt{\frac{\sum (Xi - X)^2}{n - 1}}$$

Where:
    i=from 1 to n
    n=the number of data points;
    Xi=the measured concentration value of an individual MB; and
    X=mean of the measured MB concentration values.

Third, the MDLb is then calculated as shown below:

$$MDLb = X + t_{(n-1,\ 1-\alpha=0.99)} * Sb$$

Where:
    X=mean of the MB results (zero is used in place of the mean if the mean is negative);
    $t_{(n-1,\ 1-\alpha=0.99)}$=the Student's t-value appropriate for a single-tailed $99^{th}$ percentile t statistic and a standard deviation estimate with n-1 degrees of freedom (see Table 8 below); and
    Sb=standard deviation of the MB analyses.

TABLE 8

Student's Single-Tailed $99^{th}$ Percentile t Statistic Values.

| Replicate Number n | Degrees of Freedom n − 1 | Student's t-Value $t_{(n-1,\ 0.99)}$ |
|---|---|---|
| 7 | 6 | 3.143 |
| 8 | 7 | 2.998 |
| 9 | 8 | 2.896 |
| 10 | 9 | 2.821 |
| 11 | 10 | 2.764 |
| 12 | 11 | 2.718 |
| 13 | 12 | 2.681 |
| 14 | 13 | 2.650 |
| 15 | 14 | 2.624 |
| 16 | 15 | 2.602 |
| 17 | 16 | 2.583 |
| 18 | 17 | 2.567 |
| 19 | 18 | 2.552 |
| 20 | 19 | 2.539 |
| 21 | 20 | 2.528 |

TABLE 8-continued

Student's Single-Tailed 99th Percentile t Statistic Values.

| Replicate Number n | Degrees of Freedom n − 1 | Student's t-Value $t_{(n-1, 0.99)}$ |
|---|---|---|
| 22 | 21 | 2.518 |
| 23 | 22 | 2.508 |
| 24 | 23 | 2.500 |
| 25 | 24 | 2.492 |
| 26 | 25 | 2.485 |
| 27 | 26 | 2.479 |
| 28 | 27 | 2.473 |
| 29 | 28 | 2.467 |
| 30 | 29 | 2.462 |
| 31 | 30 | 2.457 |
| 32 | 31 | 2.453 |
| 33 | 32 | 2.449 |
| 34 | 33 | 2.445 |
| 35 | 34 | 2.441 |
| 36 | 35 | 2.438 |
| 37 | 36 | 2.434 |
| 38 | 37 | 2.431 |
| 39 | 38 | 2.429 |
| 40 | 39 | 2.426 |
| 41 | 40 | 2.423 |
| 42 | 41 | 2.421 |
| 43 | 42 | 2.418 |
| 44 | 43 | 2.416 |
| 45 | 44 | 2.414 |
| 46 | 45 | 2.412 |
| 47 | 46 | 2.410 |
| 48 | 47 | 2.408 |
| 49 | 48 | 2.407 |
| 50 | 49 | 2.405 |
| 51 | 50 | 2.403 |
| 52 | 51 | 2.402 |
| 53 | 52 | 2.400 |
| 54 | 53 | 2.399 |
| 55 | 54 | 2.397 |
| 56 | 55 | 2.396 |
| 57 | 56 | 2.395 |
| 58 | 57 | 2.394 |
| 59 | 58 | 2.392 |
| 60 | 59 | 2.391 |
| 61 | 60 | 2.390 |
| 62 | 61 | 2.389 |
| 63 | 62 | 2.388 |
| 64 | 63 | 2.387 |
| 65 | 64 | 2.386 |
| 66 | 65 | 2.385 |
| 67 | 66 | 2.384 |
| 68 | 67 | 2.383 |
| 69 | 68 | 2.382 |
| 70 | 69 | 2.382 |
| 71 | 70 | 2.381 |
| 72 | 71 | 2.380 |
| 73 | 72 | 2.379 |
| 74 | 73 | 2.379 |
| 75 | 74 | 2.378 |
| 76 | 75 | 2.377 |
| 77 | 76 | 2.376 |
| 78 | 77 | 2.376 |
| 79 | 78 | 2.375 |
| 80 | 79 | 2.374 |
| 81 | 80 | 2.374 |
| 82 | 81 | 2.373 |
| 83 | 82 | 2.373 |
| 84 | 83 | 2.372 |
| 85 | 84 | 2.372 |
| 86 | 85 | 2.371 |
| 87 | 86 | 2.370 |
| 88 | 87 | 2.370 |
| 89 | 88 | 2.369 |
| 90 | 89 | 2.369 |
| 91 | 90 | 2.368 |
| 92 | 91 | 2.368 |
| 93 | 92 | 2.368 |
| 94 | 93 | 2.367 |
| 95 | 94 | 2.367 |
| 96 | 95 | 2.366 |
| 97 | 96 | 2.366 |
| 98 | 97 | 2.365 |
| 99 | 98 | 2.365 |
| 100 | 99 | 2.365 |
| 101 | 100 | 2.364 |
| ∞ | ∞ | 2.326 |

An example of an MDL study for GenX is shown in Table 9 using 75 μL injection volumes.

TABLE 9

Example of a GenX MDL study.

| | | | | | | | | | | | | | |
|---|---|---|---|---|---|---|---|---|---|---|---|---|---|
| Preparation/Analysis Date # 1 & Run Data Files | Jan. 30, 2018 | 14 | 15 | 16 | NA | NA | NA | NA | | | | | |
| Preparation/Analysis Date # 1 & Run Data Files | Jan. 31, 2018 | NA | NA | NA | 14 | 15 | NA | NA | | | | | |
| Preparation/Analysis Date # 1 & Run Data Files | Feb. 1, 2018 | NA | NA | NA | NA | NA | 14 | 15 | | | | | |

| Analyte | Spiked Conc. [μg/L] | Observed Concentration | | | | | | | Mean Conc. [μg/L] | R [%] | (Ss) [μg/L] | MDLs [μg/L] | RL [μg/L] |
|---|---|---|---|---|---|---|---|---|---|---|---|---|---|
| | | MDL [μg/L] | MDL [μg/L] | MDL [μg/L] | MDL [μg/L] | MDL [μg/L] | MDL [μg/L] | MDL [μg/L] | | | | | |
| GenX | 0.0050 | 0.00450 | 0.00527 | 0.00427 | 0.00621 | 0.00603 | 0.00574 | 0.00558 | 0.0054 | 108.3 | 0.00069 | 0.0022 | 0.010 |
| Data points count: | | 1 | 2 | 3 | 4 | 5 | 6 | 7 | | | | | |

In general, an MDL verification is performed each time an MDL study is performed and on an annual basis. In one scenario, if an MDL value is greater than or equal to the concentration used for the MDL study, the concentration used for MDL study will be the MDL verification concentration. In another scenario, if an MDL value is less than the concentration used for MDL study, a laboratory standard is prepared and analyzed in reagent water (with preservatives if applicable), wherein the, laboratory standard prepared has an analyte concentration:
 i) greater than or equal to the MDL value;
 ii) no more than 2-3 times the MDL value;
 iii) less than the concentration used for the MDL study and the RL; and
 iv) less than or equal to the RDL if applicable.

Table 10 shows an example of a practical range of detection for GenX using 75 μL injection volumes.

TABLE 10

Example of a Practical Range of Detection for GenX.

| Analyte Name | | MDL | RDL | RL (MRL) | MCL |
|---|---|---|---|---|---|
| Trade Name | IUPAC Name | [μg/L] | [μg/L] | [μg/L] | [μg/L] |
| GenX | 2,3,3,3-Tetrafluoro-2-(1,1,2,2,3,3,3-heptafluoropropoxy) propanoic acid | 0.0022 | NA | 0.010 | 50.0 |

RDL (Required Detection Limit) detection limits are established by regulatory authority for certain analytes. The laboratory MDL values must be equal to or lower than the RDL.

RL (Reporting Limits) or MRL (Minimum Reporting Level) is the practical and routinely achievable values of analyte concentration. Reporting Limits determination is based on MDL values (see below). As used herein, there is no significant difference between the terms or abbreviations "reporting limits" or "RL," and the terms or abbreviations "minimum reporting level" or "MRL". Both terms and their abbreviations indicate practical and routinely achievable values of analyte concentration.

MCL (Maximum Contamination Limit) represents the highest concentration of analyte that is allowed in drinking water. The MCL values are established by regulatory authority. In the absence of an established MCL, 50 μg/L is typically a default limit for PFAS.

In this example with the method and system described supra, GenX is detectable in water when the concentration of GenX is at least 0.0022 μg/L using a 75 μL injection volume. This means that GenX is detectable in water if GenX has a concentration of 2.2 ppt or better with a 75 μL injection volume. In terms of GenX amount, at least $1.7 \times 10^{-7}$ μg of GenX in a single injection is detectable for any injection involving, for example, an injection volume between approximately 1 μL and 100 μL.

In this example with the method and system described supra, a GenX concentration in water is determinable when the concentration of GenX is at least 0.010 μg/L using a 75 μL injection volume. This means that a concentration of GenX of 10 ppt in water is determinable with a 75 μL injection volume. In terms of GenX amount, at least $7.5 \times 10^{-7}$ μg of GenX in a single injection is quantifiable for any injection involving, for example, an injection volume between approximately 1 μL and 100 μL.

Determination of RL/MRL

In an embodiment, the RL (or MRL) is established for each method/analyte using its calculated MDL value. In this embodiment, the RL/MRL is set at a value of 1 to 5 times the MDL value and then this set RL/MRL value is confirmed as described below. In another embodiment, the RL/MRL may be set at a Required Detection Limit (RDL), which is a limit that is set by a regulatory authority. In this case, the RL/MRL based on the RDL is still confirmed in the same way as an RL/MRL based on the calculated MDL value (as described below).

The RL/MRL is confirmed by processing and analyzing seven replicates of laboratory fortified blanks (LFB) that are fortified with analyte at or below the set RL/MRL concentration. The LFB also include all method-specified dechlorination agents (e.g., ammonium chloride) and preservatives, which are included in typical sample preparation.

First, the results of the analytical run are used to determine the mean concentrations of the LFB and their standard deviations.

Second, the Half Range for the prediction interval of results ($HR_{PIR}$) are calculated using the following equation:

$$HR_{PIR} = 3.963 XS$$

Where:
 S=standard deviation of the seven LFB concentration measurements; and
 3.963 is the factor specific to seven replicates.

An upper and lower limit of the Prediction Interval of Result (PIR=Mean±$HR_{PIR}$) provides confirmation of the set RL/MRL if it meets two criteria: The Upper PIR Limit ($PIR_{UL}$) must be ≤150% recovery and The Lower PIR Limit ($PIR_{LL}$) must be ≥50% recovery for the RL/MRL to be confirmed. The calculations for $PIR_{UL}$ and $PIR_{LL}$ are as follows:

$$PIR_{UL} = \frac{Mean + HP_{PIR}}{Fortified\ Concentration} \times 100 \leq 150\%$$

$$PIR_{LL} = \frac{Mean - HP_{PIR}}{Fortified\ Concentration} \times 100 \geq 50\%$$

In various embodiments using a 75 μL injection volume, the LC/MS/MS method and system as described herein is used to detect GenX in aqueous samples with concentrations of GenX as low as approximately 0.0022 μg/L (i.e., the calculated value of the MDL). In various embodiments using a 75 μL injection volume, the LC/MS/MS method and system as described herein is used to detect GenX in aqueous samples with concentrations of GenX as low as approximately 2.2 ppt. In various embodiments, the LC/MS/MS method and system as described herein is used to detect GenX in an injection volume between approximately 1 μL and 100 μL that contains at least approximately $1.7 \times 10^{-7}$ μg of GenX. In particular, the LC/MS/MS method and system set with the parameters shown in Table 4 on an AGILENT 6490 or AGILENT 6495 mass spectrometer are shown to detect levels of GenX in aqueous samples with concentrations of GenX as low as approximately 0.0022 μg/L.

In various embodiments using a 75 μL injection volume, the LC/MS/MS method and system as described herein is used to determine concentration levels of GenX in aqueous samples with concentrations of GenX as low as approximately 0.010 μg/L (i.e., the value of the RL or MRL). In various embodiments using a 75 μL injection volume, the LC/MS/MS method and system as described herein is used to determine concentration levels of GenX in aqueous samples with concentrations of GenX as low as approximately 10 ppt. In various embodiments, the LC/MS/MS method and system as described herein is used to determine an amount of GenX in an injection volume between approximately 1 µL and 100 µL that contains at least approximately $1.7 \times 10^{-7}$ µg of GenX. In particular, a LC/MS/MS method and system set with the parameters shown in Table 4 on an AGILENT 6490 or AGILENT 6495 mass spectrometer are shown to determine concentration levels of GenX in aqueous samples with concentrations of GenX as low as approximately 0.010 µg/L.

In various embodiments, an LC/MS/MS method and system as described herein is used to determine concentration levels of GenX in aqueous samples with concentrations of GenX as low as approximately 0.010 µg/L when the ESI gas temperature setting is approximately 120° C. to approximately 160° C. on an AGILENT 6490 or AGILENT 6495 mass spectrometer.

In various embodiments, an LC/MS/MS method and system as described herein is used to determine concentration levels of GenX in aqueous samples with concentrations of GenX as low as approximately 0.010 µg/L when the ESI sheath gas heater setting is approximately 150° C. to approximately 275° C. on an AGILENT 6490 or AGILENT 6495 mass spectrometer.

In various embodiments, an LC/MS/MS method and system as described herein is used to determine concentration levels of GenX in aqueous samples with concentrations of GenX as low as approximately 0.010 µg/L when the ESI sheath gas flow is approximately 6 L/min to approximately 11 L/min on an AGILENT 6490 or AGILENT 6495 mass spectrometer.

In various embodiments as described above using a 75 µL injection volume, the LC/MS/MS method and system as described herein is used to determine concentration levels of GenX in aqueous samples with concentrations of GenX as low as approximately 0.010 µg/L and as high as approximately 1.0 µg/L. In various embodiments as described above using a 75 µL injection volume, the LC/MS/MS method and system as described herein is used to determine concentration levels of GenX in aqueous samples with concentrations of GenX as low as approximately 10 ppt and as high as approximately 1000 ppt. In various embodiments as described above, the LC/MS/MS method and system as described herein is used to determine amounts of GenX in an injection volume between approximately 1 µL and approximately 100 µL that contains approximately $1.7 \times 10^{-7}$ µg to $1.7 \times 10^{-5}$ of GenX. It will be readily apparent by a person of skill in the art that samples which are too concentrated for accurate concentration determination using methods and systems described herein, are diluted so that the diluted concentrations are accurately measured. The original sample concentrations are then calculated based well-known equations for doing so, e.g. $M_1 V_1 = M_2 V_2$.

In step 145, samples from various sources of water are collected and analyzed using the above described method. In an example, samples are collected in 250 mL polypropylene bottles. In another example, the 250 mL bottles are pre-charged with approximately 50 mg of ammonium chloride.

In an example for the analysis of GenX in tap water, the water tap is allowed to run freely until the water temperature has stabilized, and the flow is reduced to permit bottle filling without splashing. The bottle is filled to the neck, taking care not to flush out the ammonium chloride, if present. The bottle is then capped and agitated to dissolve the ammonium chloride, if present, and placed in a cooler with frozen gel packs.

In some embodiments, the samples received at the laboratory on the collection day are transported in coolers with frozen gel packs and their temperature is maintained between 1° C. and 10° C. for the first 48 hours.

In other embodiments, the samples that will not be received at the laboratory on the day of collection are maintained at a temperature range between approximately 1° C. to 6° C. until analysis is initiated at a receiving laboratory.

In some embodiments, a maximum holding time from collection to analysis is 14 days.

In various embodiments, samples are prepared for analysis by removing from refrigeration and allowing the samples to equilibrate to ambient temperature. In some embodiments, the samples are checked for dechlorination efficiency by testing with free chlorine strips to ensure that the free chlorine level is <0.1 mg/L. Samples, standards, and QCs are next loaded into 2 mL autosampler vials. In some embodiments, the samples and QCs are spiked with 10 µL of internal standard.

The samples are then analyzed by injection alongside the standards and QCs into an LC/MS/MS with ESI using the conditions described supra.

In an example, after the initial calibration is confirmed valid with the QCS and CCV, analyzing field and QC samples is typically begun at the frequency outlined in Table 11 below. The instrument's MASS HUNTER software is used in the calibration procedure.

TABLE 11

Example of Confirmation of Initial Calibration for GenX.

| Analysis # | Sample Name | QCs, ICSs, CCVs Acceptance Criteria | Int. Std. | QC and Instrument Calibration Frequency |
|---|---|---|---|---|
| 1 | ICS 1 | 1. Instrument Calibration is updated and recalculated against the newly generated calibration curve. | Internal Standard Response Relative Percent Deviation (ISRPD) must be ±50%. | Analyzed with every analytical run. |
| 2 | ICS 2 | | | |
| 3 | ICS 3 | 2. Each analyte in each calibration point, except for the concentrations ≤RL, must calculate to be ±30% of the true value. | | |
| 4 | ICS 4 | | | |
| 5 | ICS 5 | | | |
| 6 | ICS 6 | 3. Each analyte in calibration points at concentrations ≤RL must calculate to be ±50% of the true value. | | |
| 7 | ICS 7 | | | |
| 8 | QCS | 1. Recovery for target analytes must be ±30% of the true value. | | Analyzed every time an instrument calibration is run at the beginning of an analytical run. |
| 9 | CCV LL | 1. Recovery for target analytes must be ±50% of the true value. | | Analyzed at the beginning of an analytical batch. |
| 10 | MB | 1. Must be free from contamination that could prevent the determination of any target analyte. 2. Concentration of target analytes must be ≤⅓ RL. | | Analyzed with each batch of up to 20 samples processed as a group within a work shift. |

TABLE 11-continued

Example of Confirmation of Initial Calibration for GenX.

| Analysis # | Sample Name | QCs, ICSs, CCVs Acceptance Criteria | Int. Std. | QC and Instrument Calibration Frequency |
|---|---|---|---|---|
| 11 | Sample 1 | | | |
| 12 | LFM | LFM/D: Recovery for target analytes should be ±40% of the true value; precision as RPD should be ≤30%. | | Analyzed with each batch of up to 20 samples processed as a group within a work shift. |
| 13 | LFMD | | | |
| 14 | Sample 2 | | | |
| 15 | Sample 3 | | | |
| 16 | Sample 4 | | | |
| 17 | Sample 5 | | | |
| 18 | Sample 6 | | | |
| 19 | Sample 7 | | | |
| 20 | Sample 8 | | | |
| 21 | Sample 9 | | | |
| 22 | Sample 10 | | | |
| 23 | CCV ML | 1. Recovery for target analytes must be ±30% of the true value | | Analyzed with each analytical batch of up to 20 samples after the first 10 samples. |
| 24 | Sample 11 | | | |
| 25 | Sample 12 | | | |
| 26 | Sample 13 | | | |
| 27 | Sample 14 | | | |
| 28 | Sample 15 | | | |
| 29 | Sample 16 | | | |
| 30 | Sample 17 | | | |
| 31 | Sample 18 | | | |
| 32 | Sample 19 | | | |
| 31 | Sample 20 | | | |
| 32 | CCV HL | 1. Recovery for target analytes must be ±30% of the true value | | Analyzed with each analytical batch of up to 20 samples after the second 10 samples. |

RL = reporting limits.

In this example, MASS HUNTER analytical software uses peak areas and the internal standard technique to calculate concentrations of the method analytes. Data may be fit with either a linear or quadratic regression with weighting if necessary.

In this example, the percent recovery calculation for CCV, LFB, QCS and LFM is performed using the following formula:

$$P = \frac{A - B}{T} \times 100\%$$

Where:
P=percent recovery;
A=measured concentration of analyte after spiking;
B=measured background concentration of analyte; and
T=true concentration of the spike.

In this example, relative percent difference for the fortified matrix duplicate is calculated using the following formula:

$$RPD = \frac{|LFM - LFMD|}{\frac{LFM + LFMD}{2}} \times 100\%$$

Where:
RPD=relative percent difference;
LFM=measured concentration of analyte in the fortified sample; and
LFMD=measured concentration of analyte in the fortified sample duplicate.

In this example, Internal Standard Response Relative Percent Deviation (ISRPD) is calculated as follows:

$$ISRPD = \frac{IS \text{ Response in the Sample} - \text{Average } IS \text{ Response in the Initial Calibration}}{\text{Average } IS \text{ Response in the Initial Calibration}} \times 100$$

The LC/MS/MS is configured to determine a concentration of GenX as described supra. In particular, the various ESI conditions described above in the detailed embodiments are utilized.

The LC/MS/MS outputs data that allows the determination of a concentration of GenX within the unconcentrated sample, wherein the concentration of GenX within the unconcentrated sample has a minimum reporting level of approximately 0.010 µg/L.

Figure 2:
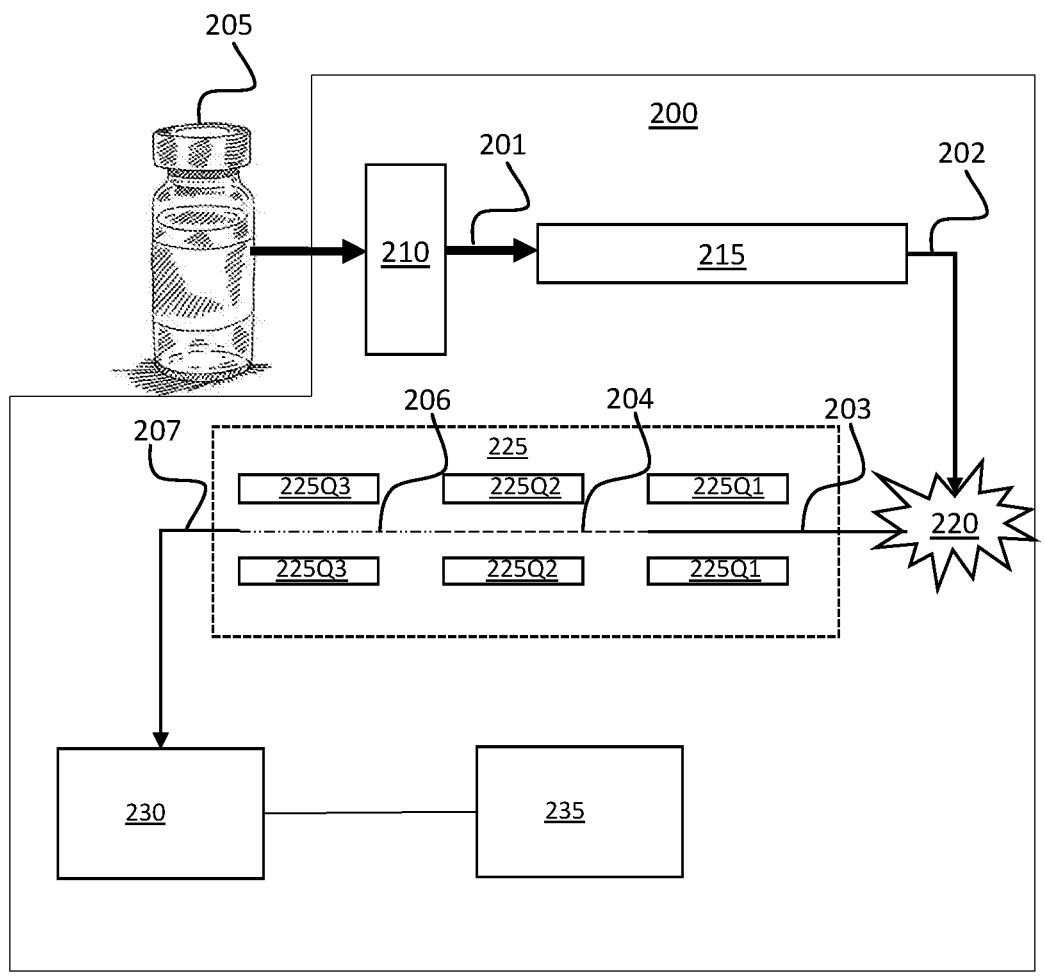
FIG. 2 depicts a block diagram of components of an LC/MS/MS system used to determine levels of GenX in samples, in accordance with an exemplary embodiment of the present invention.

FIG. 2 depicts a block diagram of components 200 of an LC/MS/MS system used to determine levels of GenX in samples in accordance with an exemplary embodiment of the present invention. It should be appreciated that FIG. 2 provides only an illustration of one implementation and does not imply any limitations with regard to other systems in which embodiments of the present invention may be implemented. Other modifications to the depicted system may be made without departing from the scope of the present invention.

LC/MS/MS system 200 includes injector 210, LC column 215, ESI ionizer component 220, triple quadrupole mass spectrometer (TQMS) component 225, ion detector 230, and mass spectrum read-out software 235.

TQMS 225 includes two quadrupole mass analyzers in series (225Q1 and 225Q3) with a non-mass-resolving quadrupole (225Q2) between them to act as a cell for collision-induced dissociation. All three quadrupole mass analyzers consist of four cylindrical rods (for reasons of simplicity they are schematically represented by the labeled parallel bars in FIG. 2.). The four cylindrical bars are set parallel to each other. For 225Q1 and 225Q3, each opposing rod pair is connected together electrically and a radio frequency (RF) voltage with a DC offset voltage is applied between one pair of rods and the other. Ions travel down the quadrupole between the rods. Only ions of a certain mass-to-charge ratio will reach detector 230 for a given ratio of voltages. Other ions have unstable trajectories and will collide with the rods. This permits selection of an ion with a particular m/z or allows the operator to scan for a range of m/z-values by continuously varying the applied voltage. Quadrapole 225Q2 is an RF-only quadrupole (non-mass filtering) for collision induced dissociation of selected parent ion(s) from 225Q1. Subsequent fragments are passed through to 225Q3 where they may be filtered or fully scanned.

In an embodiment, an aliquot of GenX sample 205 is injected into injector 210 and the injection liquid 201 is separated from other non-GenX analytes by LC column 215 using, for example, the column, conditions, and gradient example shown and described for Table 5.

After eluting through LC column 215, the GenX-containing eluent 202 is subjected to ESI 220. As stated supra and reiterated here, ESI is a technique used in mass spectrometry to produce ions using an electrospray in which a high voltage is applied to a liquid to create an aerosol that is ionized. Conditions for ionization of GenX using the ESI techniques as embodied by ESI 220 have been detailed and described supra in embodiments of the present invention.

After ionization of the GenX-containing eluent by ESI 220, the ion(s) 203 are passed through the first quadrupole mass analyzer, 225Q1, which serves as a filter for selecting desired GenX ions 204. The second quadrupole mass analyzer, 225Q2, allows for collision of selected ions 204 to produce one or more children ions 206 that then pass through the third quadrupole mass analyzer, 225Q3. Quadrupole mass analyzer 225Q3 provides a scan of the entire m/z range of the product ion(s) 206, providing output 207 for fragments 206. Quantification of selected ion 204 can then be deduced from the ion fragmentation output 207 received by ion detector 230 and processed by mass spectrum read-out software 235.

It should be appreciated that all combinations of the foregoing embodiments and additional embodiments discussed in greater detail herein (provided such embodiments are not mutually inconsistent) are contemplated as being part of the inventive subject matter disclosed herein. In particular, all combinations of claimed subject matter appearing at the end of this disclosure are contemplated as being part of the inventive subject matter disclosed herein.

Although the invention has been described by reference to specific examples, it should be understood that numerous changes may be made within the spirit and scope of the inventive concepts described. Accordingly, it is intended that the disclosure not be limited to the described examples, but that it have the full scope defined by the language of the following claims.

The invention claimed is:

1. A method for detecting GenX in an unconcentrated sample comprising:
    injecting an unconcentrated sample into an LC/MS/MS system that is configured to determine a concentration of GenX within the unconcentrated sample, wherein the LC/MS/MS includes ESI;
    subjecting the unconcentrated sample to the following ESI conditions:
        i) a probe gas temperature of approximately 120° C. to approximately 160° C.;
        ii) a sheath gas heater setting of approximately 150° C. to approximately 275° C.; and
        iii) a sheath gas flow of approximately 6 L/min to approximately 11 L/min; and
    determining the concentration of GenX within the unconcentrated sample, wherein the concentration of GenX within the unconcentrated sample is at least approximately 0.010 µg/L.

2. The method of claim 1, wherein the concentration of GenX within the unconcentrated sample is between approximately 0.010 µg/L to approximately 1.0 µg/L.

3. The method of claim 1, wherein the unconcentrated sample is subjected to the following ESI conditions:
    i) a probe gas temperature of approximately 120° C.;
    ii) a sheath gas heater setting of approximately 150° C.; and
    iii) a sheath gas flow of approximately 6 L/min.

4. The method of claim 2, wherein the unconcentrated sample is subjected to the following ESI conditions:
    i) a probe gas temperature of approximately 120° C.;
    ii) a sheath gas heater setting of approximately 150° C.; and
    iii) a sheath gas flow of approximately 6 L/min.

5. The method of claim 3 further comprising subjecting the unconcentrated sample to the following ESI conditions:
    i) a negative ion polarity setting;
    ii) a gas flow setting of approximately 11 L/min;
    iii) a nebulizer setting of approximately 20 psi;
    iv) a capillary voltage setting of approximately 3000 V;
    v) a voltage charging setting of 0; and
    vi) the following ion-funnel parameters: approximate high pressure RF=90 and approximate low pressure RF=60.

6. The method of claim 4 further comprising subjecting the unconcentrated sample to the following ESI conditions:
    i) a negative ion polarity setting;
    ii) a gas flow setting of approximately 11 L/min;
    iii) a nebulizer setting of approximately 20 psi;
    iv) a capillary voltage setting of approximately 3000 V;
    v) a voltage charging setting of 0; and
    vi) the following ion-funnel parameters: approximate high pressure RF=90 and approximate low pressure RF=60.

7. The method of claim 5, further comprising:
    detecting GenX within a second unconcentrated sample, wherein a second concentration of GenX within the second unconcentrated sample is at least approximately 0.0022 µg/L.

8. The method of claim 1, wherein an amount of GenX in a single injection of unconcentrated sample is at least approximately $7.5 \times 10^{-7}$ µg.

9. The method of claim 2, wherein an amount of GenX in a single injection of unconcentrated sample is between approximately $7.5 \times 10^{-7}$ µg to approximately $7.5 \times 10^{-5}$ µg.

10. A GenX detection system comprising:
    an LC/MS/MS system operable utilizing ESI and configured to:
        receive an injection of a unconcentrated sample containing GenX;
        subject the unconcentrated sample to the following ESI conditions:
            i) a probe gas temperature of approximately 120° C. to approximately 160° C.;
            ii) a sheath gas heater setting of approximately 150° C. to approximately 275° C.; and iii) a sheath gas flow of approximately 6 L/min to approximately 11 L/min; and determine a concentration of GenX within the unconcentrated sample, wherein the concentration of GenX within the unconcentrated sample is at least approximately 0.010 μg/L.

11. The system of claim 10, wherein the concentration of GenX within the unconcentrated sample is between approximately 0.010 μg/L to approximately 1.0 μg/L.

12. The system of claim 10, wherein the unconcentrated sample is subject to the following ESI conditions:
i) a probe gas temperature of approximately 120° C.;
ii) a sheath gas heater setting of approximately 150° C.; and
iii) a sheath gas flow of approximately 6 L/min.

13. The system of claim 11, wherein the unconcentrated sample is subject to the following ESI conditions:
i) a probe gas temperature of approximately 120° C.;
ii) a sheath gas heater setting of approximately 150° C.; and
iii) a sheath gas flow of approximately 6 L/min.

14. The system of claim 12, wherein the unconcentrated sample is subject to the following ESI conditions:
i) a negative ion polarity setting;
ii) a gas flow setting of approximately 11 L/min;
iii) a nebulizer setting of approximately 20 psi;
iv) a capillary voltage setting of approximately 3000 V;
v) a voltage charging setting of 0; and
vi) the following ion-funnel parameters: approximate high pressure RF=90 and approximate low pressure RF=60.

15. The system of claim 13, wherein the unconcentrated sample is subject to the following ESI conditions:
i) a negative ion polarity setting;
ii) a gas flow setting of approximately 11 L/min;
iii) a nebulizer setting of approximately 20 psi;
iv) a capillary voltage setting of approximately 3000 V;
v) a voltage charging setting of 0; and
vi) the following ion-funnel parameters: approximate high pressure RF=90 and approximate low pressure RF=60.

16. The system of claim 14, wherein the LC/MS/MS system is configured to detect GenX within a second unconcentrated sample that is at least approximately 0.0022 μg/L.

17. The system of claim 10, wherein an amount of GenX in a single received injection of unconcentrated sample is at least approximately $7.5 \times 10^{-7}$ μg.

18. The system of claim 11, wherein an amount of GenX in a single received injection of unconcentrated sample is between approximately $7.5 \times 10^{-7}$ μg to approximately $7.5 \times 10^{-5}$ μg.

19. A method for detecting GenX in a solution comprising:
injecting a solution containing GenX into an LC/MS/MS system that is configured to detect GenX within the solution, wherein the LC/MS/MS includes ESI;
subjecting a GenX-containing LC eluent of the solution to the following ESI conditions:
i) a probe gas temperature of approximately 120° C. to approximately 160° C.;
ii) a sheath gas heater setting of approximately 150° C. to approximately 275° C.; and
iii) a sheath gas flow of approximately 6 L/min to approximately 11 L/min; and
determining a concentration of GenX within the solution containing GenX, wherein an injected amount of GenX within the solution containing GenX is at least approximately $7.5 \times 10^{-7}$ μg.

20. The method of claim 19, wherein the injected amount of GenX within the solution containing GenX is between approximately $7.5 \times 10^{-7}$ μg to approximately $7.5 \times 10^{-5}$ μg.

* * * * *